(12) United States Patent
Saito

(10) Patent No.: US 11,480,539 B2
(45) Date of Patent: Oct. 25, 2022

(54) METHOD FOR MEASURING MEMBRANE POTENTIAL/MEMBRANE CURRENT OF CELL

(71) Applicant: Ion Chat Research Corporate, Wako (JP)

(72) Inventor: Mitsuyoshi Saito, Tokyo (JP)

(73) Assignee: Ion Chat Research Corporate, Wako (JP)

( * ) Notice: Subject to any disclaimer, the term of this patent is extended or adjusted under 35 U.S.C. 154(b) by 469 days.

(21) Appl. No.: 16/609,140

(22) PCT Filed: Apr. 27, 2018

(86) PCT No.: PCT/JP2018/017334
§ 371 (c)(1),
(2) Date: Oct. 28, 2019

(87) PCT Pub. No.: WO2018/199334
PCT Pub. Date: Nov. 1, 2018

(65) Prior Publication Data
US 2021/0102911 A1 Apr. 8, 2021

(30) Foreign Application Priority Data

Apr. 28, 2017 (JP) .............................. JP2017-090632

(51) Int. Cl.
*G01N 27/30* (2006.01)
*G01N 33/543* (2006.01)
*G01N 33/68* (2006.01)

(52) U.S. Cl.
CPC ....... *G01N 27/30* (2013.01); *G01N 33/54326* (2013.01); *G01N 33/54346* (2013.01); *G01N 33/6872* (2013.01)

(58) Field of Classification Search
CPC ............ G01N 27/30; G01N 33/54326; G01N 33/54346; G01N 33/6872; G01N 33/48728; C12N 15/09; C12M 1/34; C12Q 1/02
See application file for complete search history.

(56) References Cited

U.S. PATENT DOCUMENTS

2004/0146849 A1* 7/2004 Huang ............. G01N 33/48728
435/287.1
2007/0092865 A1 4/2007 Lynch et al.
(Continued)

FOREIGN PATENT DOCUMENTS

JP 2005-505761 A 2/2005
JP 2012-503492 A 2/2012
(Continued)

OTHER PUBLICATIONS

Silva, et al., "Gold Coated Magnetic Nanoparticles: From Preparation to Surface Modification for Analytical and Biomedical Applications", Chem. Commun. 2016, 52, 7528.
(Continued)

*Primary Examiner* — Jennifer Wecker
*Assistant Examiner* — Alea N. Martin
(74) *Attorney, Agent, or Firm* — Fox Rothschild LLP

(57) ABSTRACT

The purpose of the present invention is to provide a method for accurately measuring and controlling intracellular potential by a simple method that is less invasive to the cell and does not require a skilled technique. The present invention makes it possible to provide an intracellular recording electrode inside the cytoplasm by introducing conductive nanoparticles into a cell cultured on a conductive plate electrode, attracting the conductive nanoparticles inside the cell to the side of the cell adhered to the conductive plate (Continued)

electrode, and causing the conductive nanoparticles to pass through the cell membrane. Measuring the current or voltage between the intracellular recording electrode and an extracellular electrode in extracellular solution makes it possible to measure the intracellular potential. In addition, applying a current from one of the electrodes or applying a voltage makes it possible to control the intracellular potential and to measure the activity of the ion channels using a membrane potential fixation method. Similarly, using a magnetic electrode adhered to the cell surface of a target cell into which conductive nanoparticles have been introduced beforehand to attract the conductive nanoparticles in the cell to the side of the cell adhered to the electrode and cause the conductive nanoparticles to pass through the cell membrane to make contact with the magnetic electrode, makes it possible to provide an intracellular recording electrode inside the cytoplasm. Alternatively, adhering conductive nanoparticles adsorbed to the surface of a magnetic electrode to the upper side of the target cell and causing the conductive nanoparticles to pass through the cell membrane by attracting the conductive particles to an iron plate provided on the lower side of the cell thereby forms an intracellular recording electrode.

16 Claims, 10 Drawing Sheets

Specification includes a Sequence Listing.

(56) References Cited

U.S. PATENT DOCUMENTS

| | | |
|---|---|---|
| 2010/0304425 A1 | 12/2010 | Speller |
| 2011/0286975 A1 | 11/2011 | Souza et al. |
| 2012/0034622 A1 | 2/2012 | Ignatius et al. |
| 2013/0230881 A1 | 9/2013 | Yasuda et al. |
| 2014/0349332 A1 | 11/2014 | Yasuda et al. |
| 2016/0011176 A1 | 1/2016 | Yasuda et al. |

FOREIGN PATENT DOCUMENTS

| | | |
|---|---|---|
| WO | 2012/043820 A1 | 4/2012 |
| WO | 2013/061849 A1 | 5/2013 |
| WO | 2014 098182 A1 | 6/2014 |

OTHER PUBLICATIONS

Gramowski, et al., "Nanoparticles Induce Changes of the Electrical Activity of Neuronal Networks on Microelectrode Array Neurochips", Environ Health Perspect, 2010, vol. 118, pp. 1363-1369.

Kami, et al., "Application of Magnetic Nanoparticles to Gene Delivery", Int. J. Mol. Sci. 2011, vol. 12, pp. 3705-3722.

Kim, et al., "Multi-Electrode Arrays Modified With Bimetallic Nanoparticles; Electrical Performance and Neural Signal Recording", IEEE International Conference on Nanotechnology, Jul. 27-30, 2015.

Fendyur, et al., "Formation of Essential Ultrastructural Interface Between Cultured Hippocampal Cells and Gold Mushroom-Shaped Mea-Toward "In Cell" Recordings From Vertebrate Neurons", Frontiers in Neuroengineering, Original Research Article, Dec. 8, 2011, vol. 4, Article 14, pp. 1-14.

Spira et al., "Multi-Electrode Array Technologies for Neuroscience and Cardiology", Nature Nanotechnology, vol. 8, Feb. 2013, pp. 83-94.

Levy, et al., Gold Nanoparticles Delivery in Mammalian Live Cells: A Critical Review, Nano Reviews 2010, 1:4889, pp. 1-18.

International Search Report cited in PCT/JP2018/017334, dated Aug. 1, 2018.

Extended European Search Report of EP 18791308.2, dated Jun. 17, 2021.

Lee et al., Noninvasive Measurement of Electrical Events Associated with a Single Chlorovirus Infection of a Microalgal Cell, Chemical and Biomolecular Engineering, Department of Chemical and Biomolecular Engineering, University of Nebraska-Lincoln, Published in ACS Nano 10 (2016), pp. 5123?5130.

* cited by examiner

[FIG. 2]
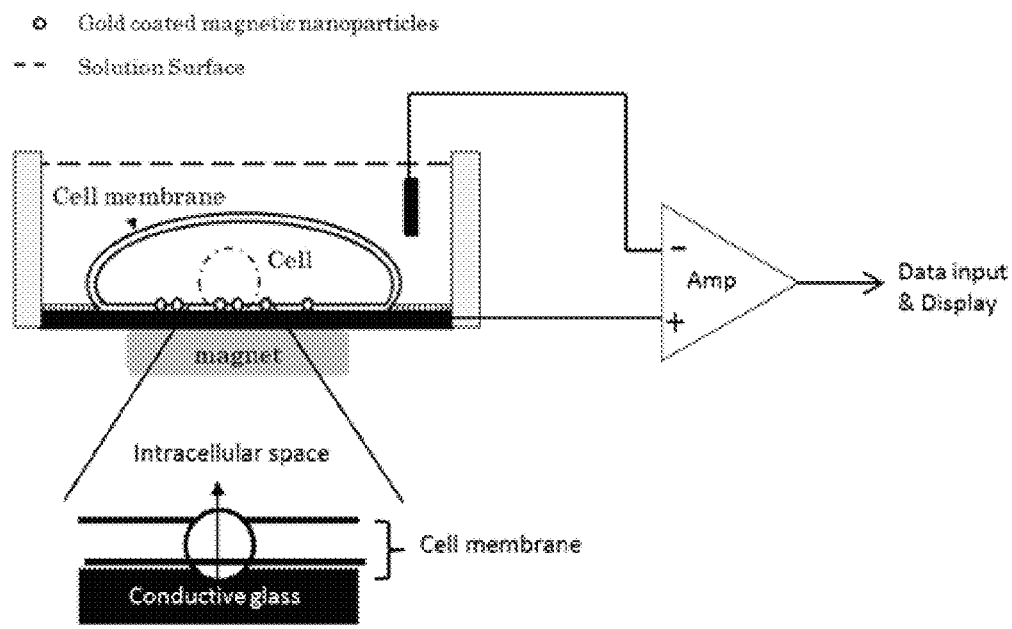
[FIG. 3]
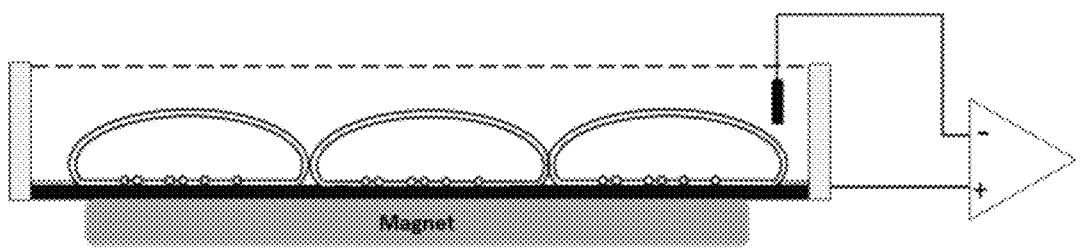

[FIG. 4]
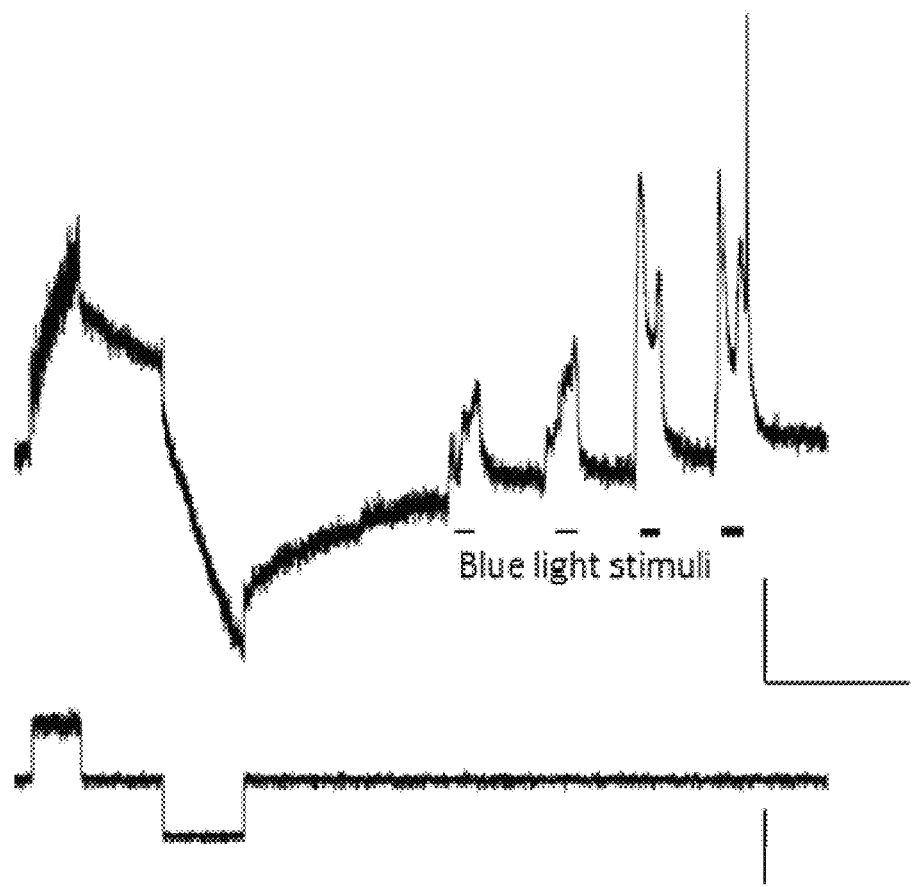

[FIG. 9]

[FIG. 11]
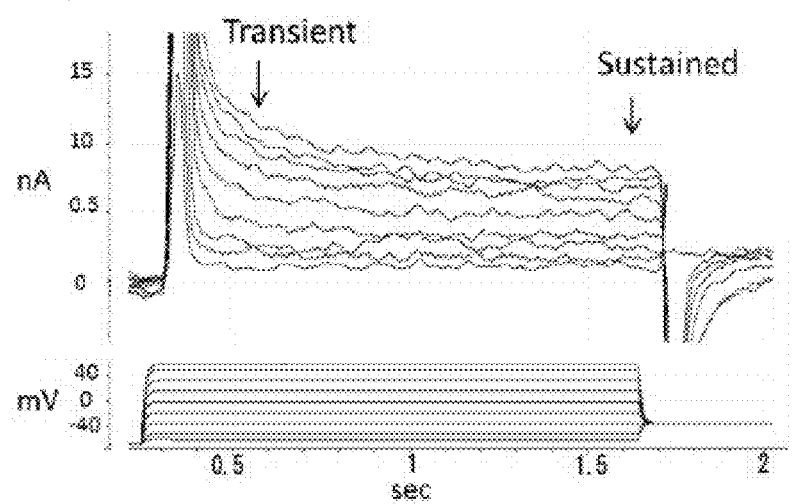
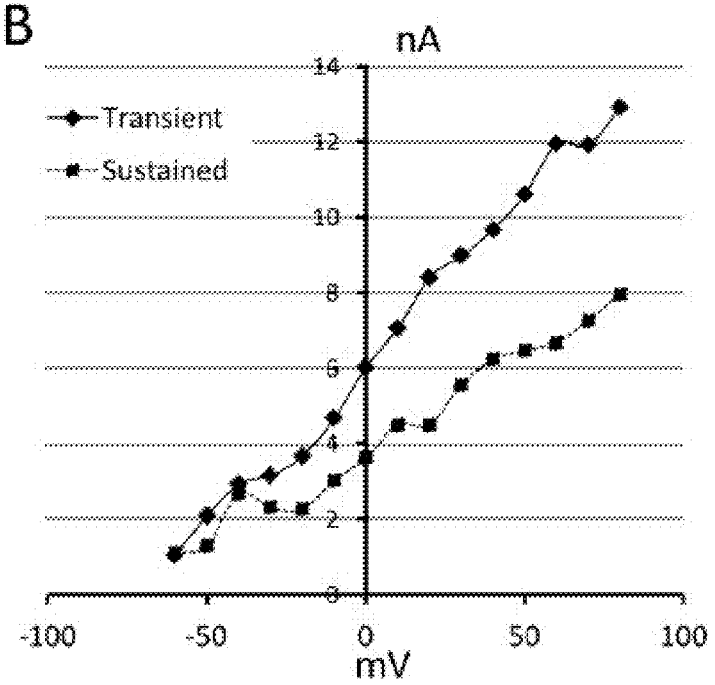

SEQUENCE LISTING

<160> NUMBER OF SEQ ID NOS: 6

<210> SEQ ID NO 1
<211> LENGTH: 38
<212> TYPE: DNA
<213> ORGANISM: Artificial Sequence
<220> FEATURE:
<223> OTHER INFORMATION: ChRWR sense primer

<400> SEQUENCE: 1
cactataggg aagctaccat ggctcggaga ccctggct                        38

<210> SEQ ID NO 2
<211> LENGTH: 38
<212> TYPE: DNA
<213> ORGANISM: Artificial Sequence
<220> FEATURE:
<223> OTHER INFORMATION: ChRWR antisense primer

<400> SEQUENCE: 2
atagaatagg aagctctact tgcctgtccc tttgttga                        38

<210> SEQ ID NO 3
<211> LENGTH: 20
<212> TYPE: DNA
<213> ORGANISM: Artificial Sequence
<220> FEATURE:

```
<223> OTHER INFORMATION: KIR2.1 1st sense primer

<400> SEQUENCE: 3
ccaaagcaga agcactggag                                                20

<210> SEQ ID NO 4
<211> LENGTH: 22
<212> TYPE: DNA
<213> ORGANISM: Artificial Sequence
<220> FEATURE:
<223> OTHER INFORMATION: KIR2.1 1st A/S

<400> SEQUENCE: 4
ctttgaaacc attgtgcttg cc                                             22

<210> SEQ ID NO 5
<211> LENGTH: 39
<212> TYPE: DNA
<213> ORGANISM: Artificial Sequence
<220> FEATURE:
<223> OTHER INFORMATION: KIR2.1 ICR HindIII sense

<400> SEQUENCE: 5
cactataggg aagctaccat gggcagtgtg cgaaccaac                           39

<210> SEQ ID NO 6
<211> LENGTH: 36
<212> TYPE: DNA
<213> ORGANISM: Artificial Sequence
<220> FEATURE:
<223> OTHER INFORMATION: KIR2.1 ICR HindIII A/S

<400> SEQUENCE: 6
atagaatagg aagcttcata tctccgactc tcgccg                              36
```

METHOD FOR MEASURING MEMBRANE POTENTIAL/MEMBRANE CURRENT OF CELL

This application is a national Phase application filed under 35 U.S.C. § 371 of PCT International Application No. PCT/JP2018/017334 with an International Filing Date of Apr. 27, 2018 which claims under 35 U.S.C. § 119(a) the benefit of Japanese Application 2017-090632 filed on Apr. 28, 2017. The entire contents of these applications are incorporated herein by reference in their entirety.

TECHNICAL FIELD

The present invention describes a method of measuring or controlling a membrane potential (intracellular potential) and a membrane current (current flowing in an ion channel present in a cell membrane) in a cell in one cell unit or cell population.

BACKGROUND ART

Ionic compositions of intracellular compartment in cells are different from extracellular compartment. This is the main cause of forming the intracellular potential (membrane potential) by keeping the difference in the ion composition is maintained by ion transporters (g, Na+/K+ ATPase, etc.). In the resting state, the membrane potential is stable (resting membrane potential), but when the ion channels on the membrane surface are activated and their open, and it opens, ions are released or flowed at once from one side to the other by the differences in ion concentrations between the inside and outside of the membrane, resulting in a change in intracellular potential (depolarization or hyperpolarization). Sudden changes in the ion composition result in action potential generation leading to signal transmission such as the release of hormones and neurotransmitters, and contraction in the myocardium and skeletal muscle cells.

Measuring changes in cell membrane potential and the resulting membrane current through ion channels is one of commonly used methods to screen effects of drugs. Particularly in drug discovery screening assays, it is a routinely used method to expose drug candidates to cultured cardiomyocytes, neurons, etc. and to measure changes in membrane potential to evaluate cardiotoxicity, neurotoxicity, etc.

In order to measure the intracellular potential, conventionally, a micro-glass electrode filled with an electrolytic solution was inserted into the cell to measure the current or voltage having the extracellular electrode as a reference point. Recently, a patch clamp method has been established and has become a standard technology for such experiments. The patch clamp method is a method of accurately measuring and controlling the intracellular potential change. By adhering a glass (patch) pipette filled with intracellular electrolyte to the cell membrane and by rapturing the patch of the membrane under the patch pipette, cellular internal space is electrically integrated with the patch pipette integrating the glass pipette with the cell. The patch clamp method is divided in various configuration. Measuring the dynamics of ion channels expressed throughout the cell is called whole cell configuration; measuring the dynamics (single channel activity) of ion channels contained only in the cell membrane within the inner diameter of the patch pipette is called on cell configuration. And, there is a cell free configuration (inside patch, outside patch configurations) where measurement of ion channel activities in the patch membrane (micromembrane that is excised (isolated) from a cell.

In the whole cell mode, the dynamics of intracellular potential change (Current-clamp) and the current passing through the ion channel throughout the cell (the activity of the ion channel, Voltage-clamp) are measured by breaking the cell membrane at the inner diameter of the electrode adhered to the glass pipette. The above procedure requires highly skilled technique and high expertise to perform experiments because precise protocol should be followed; 1. visualize a cell to record under the microscope, 2. place patch pipette on to a target cell by using a micromanipulator.

Using the intracellular recording methods (Voltage-clamp, Current-clamp) as represented by the whole-cell patch method (Whole cell patch), it is possible to observe the dynamics of ions passing through ion channels expressed (present) in the cell membrane. In the voltage-clamp mode, the feedback function included in the patch-clamp amplifier can efficiently control the potential in the cell, and the fast (millisecond unit) phenomenon that occurs due to the opening and closing of the ion channel can be recorded as the ion current change. In the current-clamp mode, the action on the cell by the activity of the ion channel can be recorded as a (membrane) potential change.

The patch clamp method includes a manual (manual) patch clamp method and an auto patch method, and the manual patch clamp method has high data reliability in electrophysiological measurement. However, this method is very inefficient because the procedure is complicated and requires a lot of expertise such as operating the manipulator under a microscope. This is a major hurdle in medical biology research, particularly in the field of drug discovery.

On the other hand, the auto patch method is an automated electrophysiological measurement machine, and although its performance has been significantly improved in recent years, the reliability of data has not reached the level replace the manual patch clamp method. In addition, the auto patch clamp equipment is very expensive, therefore its use is limited to some large pharmaceutical companies.

Also, in recent years, as a method of recording the intracellular potentials using multielectrode array recording system, a method of electrically perforating a cell by applying a high voltage to a cell. It has been reported that the intracellular potential of rat cardiomyocytes was successfully recorded. However, in this method, the perforated cell membrane is immediately repaired, so that the access of the electrode into the cell is lost. The observable time of the electrical response is at most about 10 minutes, which is not a practical method.

With respect to such intracellular recording methods, development of extracellular recording methods to record extracellular electrical changes has also been advanced and widely used in recent years. Extracellular recording records cellular electrical changes using electrodes placed extracellularly. in vitro multi-point planar electrode (multielectrode array) systems are based on this method (patent documents 1 to 4).

As an application of the in vitro multi electrode array (MEA) system, it is used to study plasticity of cultured neurons, to test drug safety using neurons derived from human iPS cells, and/or cardiomyocytes.

Since MEA is extracellular recording, it is much easier to perform experiments. But the information that can be gained with this method is limited. For example, slowly occurring membrane potential changes cannot be recorded. It is because extracellular recording permits only alternating current-like changes (change in unit time of membrane potential, differential waveform). Therefore, the information obtained by this measurement and its application is limited.

As an example of an attempt to make intracellular recording by a method based on MEA, there has been a case where cell membranes were successfully broken by seeding cells on a mushroom-like shaped electrode and applying a high voltage to break the cell membrane (nonpatent literature 1). It can maintain the recording condition of the intracellular potential is as short as 3 minutes or less. Therefore, it has not claimed to be an effective recording method for routine assays.

From the above reasons, there has been a strong demand. It was hoped to provide a possible method that is an easy-to-use, and stable as a extracellular recording method like MEA, and it is possible to measure the membrane potential with high accuracy equal to or more than the manual patch clamp method, and control of the intracellular potential. It was hoped to provide a possible method.

CITATION LIST

Patent Document

Patent Document 1: WO2012/043820
Patent Document 2: WO2013/061849
Patent Document 3: WO2014/098182
Patent Document 4: JP2005-505761A Non-Patent Document Non-Patent Document 1: Anna Fendyur, et al., Frontiers in Neuroengineering, December 2011, Vol. 4, Article 14, p. 1-14
Non-Patent Document 2: Raphael Levy, et al., NanoReviews 2010, 1: 4889-DOI: 10.3402/nano.v1i0.4889
Non-Patent Document 3: Micha E. Spira et al., Nature Nanotechnology Vol. 8 (February 2013) p. 83-94/DOI: 10.1038/NNANO.2012.265

SUMMARY OF THE INVENTION

Problems to be Solved by the Invention

The present invention is a method of accurately measuring the intracellular potential of a single cell unit or cell population (sheet-like cell or cell mass) by a simple method that has less invasiveness to cells and does not require a skilled procedure, and a simple method. The object of the present invention is to provide a method of controlling intracellular potential.

Means for Solving the Problems

In order to accurately measure the intracellular potential, a glass microelectrode is inserted into the cell, and it's the potential difference with the extracellular electrode (ground) is amplified through an amplifier and observed with a monitor.

Based on the following reports that gold nanoparticles are widely used not only as a kit for immunological diagnosis but also as a vehicle for delivery of nucleic acids and various drugs to mammalian cells including human cells, and the method to deliver nanoparticles to the intracellular space becomes much gentler than previous method so that the procedure can be performed with less stress to cells (Non-patent document 2). We also paid attention to the fact that gold nanoparticles have extremely low cytotoxicity and are electrically conductive. Taking into considerations the facts described above inspired us to propose a possibility that the gold nanoparticles may be able to function as the glass intracellular electrodes.

As a result of intensive studies, the present inventors discovered that transmembrane gold-coated magnetic nanoparticles can function as intracellular electrodes. Gold nanoparticles that introduced in cells, which were plated on a conductive glass plate. Then with a strong magnet intracellular nanoparticles were pulled toward the bottom of the cells and penetrated the cell membrane and became transmembrane. Portions of the nanoparticles that were exposed to the extracellular contact to the conductive glass and the other side exposed to the intracellular space sense changes in the intracellular membrane potential. Specifically, gold-coated magnetic nanoparticles are introduced in advance together with a chemical such as polyethylenimine into cultured cells adhered to the surface of a conductive glass plate, and a neodymium magnet directly under the conductive glass plate pulled gold nanoparticles to penetrate the cell membrane, and one end of the cell was brought into contact with the conductive glass, and then the potential difference between the conductive glass and the extracellular electrode (ground) was amplified by an amplifier and observed with a monitor.

As a result, it has been confirmed that the intracellular potential can be measured over 30 minutes as in the case that recordings were made using the conventional intracellular glass microelectrode.

This means that the gold-coated magnetic nanoparticles, which are conductive nanoparticles in cells, are moved toward the cell membrane by the force of magnetic fields and penetrate the cell membrane. This process is very gentle and the damage to the cells is minimum. Since the nanoparticles used have a diameter of 50 nm, which is far larger than the thickness of the cell membrane, both sides of nanoparticles are exposed to inside and outside the cells and function as an intracellular electrode. This explains the construction of the recording electrode. And this means that it has become possible to observe alterations of the intracellular potential in living cells for a long period of time using an amplifier.

Also, nanoparticle coating with other materials with low cytotoxicity and conductivity (i.e. platinum) can be considered. Also, conductive peptide, protein, polymer, etc. are consider to be possible alternatives. The same effect can be expected to be obtained by using Qdot particles used for live imaging.

The present invention is based on the above experimental results

Furthermore, the conductive nanoparticles inside the cell can be pulled toward a magnet place above the cell. A conductive metal-coated neodymium magnet on top of the cell can function as conductive glasses (see above). When conductive nanoparticles inside the cell are pulled toward a magnet and penetrate the cell membrane, they form a nanoparticle-magnet complex-magnet electrode (MagEle). By doing so, intracellular potential changes can be detected. We concluded that this nanoparticle-magnet complex can function as an intracellular recording electrode and measure the intracellular potential.

The present invention includes the following inventions.
[1] Conductive nanoparticles penetrating a cell membrane of a target cell, characterized in that one end of the conductive nanoparticles are exposed inside the cell, and the other end are exposed outside the cell.

[2] The conductive nanoparticles according to [1],
wherein one end exposed extracellularly are in contact with a conductive plate electrode or a magnet electrode.

[3] The conductive nanoparticles according to [1] or [2],
wherein the conductive nanoparticles are composed of magnetic nanoparticles coated with a conductive material.

[4] A cell characterized in that at least a part of cell membrane comprises conductive nanoparticles penetrating said cell membrane.

[5] An intracellular recording electrode comprising: conductive nanoparticles penetrating the cell membrane of target cells, and a conductive plate electrode or magnet electrode contacting with the conductive nanoparticles that are extracellularly exposed at the outside of the target cells,
wherein the intracellular recoding electrode is capable of recording the intracellular potential or potential change of the target cells.

[6] The intracellular recording electrode according to [5],
wherein the conductive plate electrode that contacts with one end of the conductive nanoparticles exposed outside the cell has a magnet attached to the opposite side of the cell contact surface of the conductive plate electrode.

[7] The intracellular recording electrode according to [6],
wherein the surface of the conductive plate electrode is covered with collagen at least in part.

In addition, it is preferable that a collagen coating film is provided in a grid|lattice form. This method is effective for HEK cells, cells with weak adhesion to conductive glass such as cultured cardiomyocytes. As fibroblasts such as CHO cells adhere on conductive glass, the above surface treatment is not necessary.

[8]. The intracellular recording electrode according to [5],
wherein the magnet electrode that contacts with one end of the conductive nanoparticles exposed to the outside of the cell is coated with a conductive substance, and all the surfaces of the magnet electrode in contact with the external liquid other than the contact surface with the conductive nanoparticles are further coated with an insulator.

[9] The intracellular recording electrode according to any one of [5] to [8],
wherein conductive nanoparticles pre-introduced in the target cells are pulled by the magnetic force from a magnet placed on the opposite side of the cell contacting surface of the conductive plate electrode or by the magnetic force from the magnet electrode to become conductive nanoparticles penetrating the cell membrane of the target cells, and
wherein one end of the conductive nanoparticles exposed extracellularly are in contact with the conductive plate electrode or the magnet electrode.

[10] The intracellular recording electrode according [5] or [8],
wherein at the contacting surface where the target cells and the magnet electrode fixed above the target cells make contact, the conductive nanoparticles penetrating the cell membrane expose their one ends extracellularly, which make contact with the magnet electrode, and expose the other ends intracellularly, and
wherein the intracellular recording electrode comprises a container with a magnet attracting metal plate equipped below the bottom surface of the container to which the target cells adhere.

[11] The intracellular recording electrode according to [10],
wherein conductive nanoparticles pre-adsorbed on the surface of the magnet electrode are pressed against the cell surface from the upper side of the target cell as well as are drawn into the cell membrane by the metal plate equipped below the target cells to form the conductive nanoparticles penetrating the cell membrane of the target cell.

[12] The intracellular recording electrode according to [11],
wherein the conductive nanoparticles pre-adsorbed on the surface of the magnet electrode are prepared using conductive nanoparticles in a pre-mixed with a transfection reagent.

Here, representative one as a transfection reagent is polyethyleneimine (PEI), but it is also possible to use Superfect (Qiagen) or the like.

[13] An apparatus for measuring and/or controlling an intracellular potential or a change in the potential of a target cell, comprising:
the intracellular recording electrode according to any of [5] to [12] is connected to the positive input of a measuring instrument, and
an apparatus in which a ground electrode placed in the extracellular solution of an intracellular potential recording container is connected to the negative input of the measuring instrument,
thereby to form a potential recording circuit.

[14] An apparatus for measuring and/or controlling an intracellular potential of the target cells comprising at least the following (A) to (E):
(A) a container containing saline solution;
(B) the intracellular recording electrode according to any one of [5] to [12];
(C) extracellular electrodes provided in saline in the container;
(D) an electrical signal measuring and/or generating device; and
(E) an electric signal amplifier.

[15] A method for measuring and/or controlling the intracellular potential or changes in the intracellular potential of a target cell comprising:
a step of introducing conductive nanoparticles into a target cell in advance; and
a step of drawing the intracellular conductive nanoparticles to the cell surface in contact with a magnet electrode or conductive plate electrode adhering to the surface of the target cells to penetrate the cell membrane by the magnetic force from the magnet electrode or the conductive plate electrode, and thereby forming an intracellular recording electrode by contacting one end of the conductive nanoparticles exposed to the outside of the target cell with the magnet electrode or conductive plate electrode.

[16] The method according to [15], comprising the following steps (1) to (5):
(1) introducing conductive nanoparticles into target cells as adhered to the bottom of a container;
(2) pulling the conductive nanoparticles in target cells, that adhere on a conductive plate electrode forming at least part of the bottom of the container, by the magnetic force from magnet placed on the opposite side in between the cells contacting surface of the conductive plate electrode to penetrate the cell membrane, and thereby contacting one end of the conductive nanoparticles exposed to the outside of the target cells with the conductive plate electrode;
(3) forming an intracellular recording electrode composed of conductive nanoparticles with one end exposed to the inside the target cells and the conductive plate electrode in contact with the one end of the conductive nanoparticles exposed to the outside of the target cells;
(4) providing an extracellular reference electrode at a position that is not in contact with cells in the physiological saline in the container; and
(5) connecting the intracellular recording electrode and the extracellular electrode to an electrical signal measuring instrument via an electrical signal amplifier, and measuring the current or voltage between the both electrodes.

[17] The method according to [15], comprising the following steps (1) to (6):

(1) introducing conductive nanoparticles into a target cell as adhered to the bottom of a container;

(2) contacting a magnet electrode to the target cell surface excluding the surface where the target cells adhere to the container;

(3) drawing the conductive nanoparticle in the target cell to the magnet electrode to penetrate the cell membrane, and thereby contacting one end of the conductive nanoparticles exposed to the outside of the target cells with the magnet electrode;

(4) forming an intracellular recording electrode composed of conductive nanoparticles with one end exposed to the inside of the target cells and magnet electrode in contact with the one end of the conductive nanoparticles exposed to the outside of the target cells;

(5) providing an extracellular reference electrode at a position that is not in contact with cells in the physiological saline in the container; and (6) connecting the intracellular recording electrode and the extracellular electrode to an electrical signal measuring instrument via an electrical signal amplifier, and measuring the current or voltage between the both electrodes.

[18] A method for measuring and/or controlling the intracellular potential or changes in the intracellular potential of a target cell comprising:

a step of holding conductive nanoparticles at the surface of the magnet electrode by magnetic force in advance; and a step of pressing the magnet electrode against the surface of the target cell and drawing the conductive nanoparticles to the metal plate provided below the cell to penetrate the cell membrane, and thereby forming an intracellular recording electrode composed of conductive nanoparticles with one end reaching inside the target cell and the magnetic electrode.

Here, the conductive nanoparticles attached the magnet electrode surface may be used alone, but when they form complex with the transfection reagent, it is more efficient in penetrating the cell membrane.

[19] A method for measuring and/or controlling the intracellular potential or changes in the intracellular potential of a target cell comprising the following steps (1) to (7):

(1) culturing target cells in a container placed on a metal plate capable of being attracted by magnetic force;

(2) adsorbing conductive nanoparticles to the surface of a magnet electrode;

(3) contacting the surface of the magnet electrode, on which the conductive nanoparticle is adsorbed, directly to the surface of the target cells in the container excluding the surface where the target cells adhere to the container;

(4) drawing conductive nanoparticles to the metal plate placed below the container, to which the cell adheres, to penetrate the cell membrane to expose one end of the conductive nanoparticles to the inside of the target cell;

(5) forming the intracellular recording electrode composed of the conductive nanoparticles having one end exposed to the inside of the target cell and the magnet electrode in contact with the one end of the conductive nanoparticles exposed to the outside of the target cell;

(6) providing an extracellular electrode at a position that is not in contact with cells in physiological saline in the container; and (7) connecting the intracellular recording electrode and the extracellular electrode to an electrical signal measuring instrument via an electrical signal amplifier, and measuring the current or voltage between both electrodes.

Here, in the step (2), the cell membrane penetration efficiency is enhanced by adsorbing the conductive nanoparticles on the surface of the magnet electrode in a state of being mixed with the transfection reagent. A representative example of the transfection reagent at that time is polyethylene imine (PEI), and it is thought that the magnetic force of the conductive nanoparticle in the step (4) helps the transmembrane of the conductive nanoparticles.

[20] The method according to any one of [15] to [19], which further comprising:

a step of controlling an intracellular potential in the target cell by applying current or voltage to the target cell using the electrical signal amplifier, in which the intracellular recording electrode and the extracellular electrode are connected, wherein in the step, the electrical signal amplifier acts as an electric signal generator.

[21] A method for screening a substance having a toxic action or an active action on a target cell comprising the following steps (1) to (6):

(1) introducing conductive nanoparticles into target cells that adhere to the bottom of a container;

(2) drawing the intracellular conductive nanoparticles to the cell surface in contact with a magnet electrode or conductive plate electrode adhering to the surface of the target cells to penetrate the cell membrane by the magnetic force from the magnet electrode or the conductive plate electrode, and thereby the conductive nanoparticles to make contact with the magnet electrode or conductive plate electrode;

(3) providing an extracellular electrode at a position that is not in contact with cells in physiological saline in a culture vessel, and measuring the current or voltage between the extracellular electrode and the intracellular recording electrode in step (2);

(4) administering a test substance sample to the target cells;

(5) measuring the current or voltage between both electrodes, in the same manner as in step (3), of the target cell to which the test substance sample is administered in step (4); and (6) comparing the measurement result in step (5) with the measurement result in step (3), and evaluating the test substance sample as a substance having a toxic action or an active action on the target cell if there is a significant difference between the two measured values.

[22] A method for screening a substance having a toxic action or an active action on a target cell comprising the following steps (1) to (9):

(1) culturing target cells in a container placed on a metal plate capable of attracted by magnetic force;

(2) adsorbing conductive nanoparticles to the surface of a magnet electrode;

(3) contacting the surface of the magnet electrode, on which the conductive nanoparticle is adsorbed directly with the upper surface of the target cell in the container;

(4) drawing conductive nanoparticles to the metal plate placed below the container, to which the cell adheres, to penetrate the cell membrane to expose one end of the conductive nanoparticles to the inside of the target cells;

(5) forming the intracellular recording electrode composed of the conductive nanoparticles having one end exposed to the inside of the target cells and the magnet electrode in contact with the one end of the conductive nanoparticles exposed to the outside of the target cells;

(6) providing an extracellular electrode at a position that is not in contact with cells in the physiological saline in a culture vessel, and measuring the current or voltage between the extracellular electrode and the intracellular recording electrode in step (5);

(7) administering a test substance sample to the target cells;

(8) measuring the current or voltage between both electrodes, in the same manner as in step (6), of the target cell to which the test substance sample is administered in step (7); and (9) comparing the measurement result in step (8) with the measurement result in step (6), and evaluating the test substance sample as a substance having a toxic effect or an active action on the target cell if there is a significant difference between the two measured values.

Here, in step (2), the conductive nanoparticles may be used alone, but when used in a state of being mixed with a transfection reagent (typically, polyethyleneimine (PEI)), the conduction by magnetic force in step (4) Cell membrane penetration of functional nanoparticles is aided.

Effects of the Invention

The present invention is based on the concept that using transmembrane magnetic conductive nanoparticles as an electrode to electrically connect inside and outside cells by attracting conductive nanoparticles, which are previously introduced into cells, with a magnetic field to penetrate cell membranes. The technology does not require specialized skills, and can be carried out easily. Additional merit of this method is minimizing the damage to the cells by not physically breaking the cell membranes, allowing long term recordings (~1 hour) of the changes in the intracellular potential. So to speak, the conductive nanoparticles acted like micro glass electrodes, allowing the potential difference inside and outside the cell through the cell membrane. Therefore, by using nanoparticles (electrodes), it has become possible to appropriately control the intracellular potential.

Further, according to the present invention, the intracellular potential in individual cells and the intracellular potential in a cell aggregate such as a cell sheet can also be measured.

For example, by applying the present invention to transformed cells or cell groups expressing various ion channels, drug transporters, etc., changes in intracellular potential due to the addition of various drugs can be observed. It can be a tool for screening efficacy or cytotoxicity test compounds.

BRIEF DESCRIPTION OF DRAWINGS

FIG. 2 Conceptual diagram showing measurement of intracellular potential by extracellular device (recording electrode, earth, amplification amplifier)

FIG. 3 The conceptual diagram at the time of applying with respect to the cell population seeded on the conductive plate surface.

FIG. 4 Voltage response to blue light stimulation on hChRWR expressing CHO cultured cells with gold coated magnetic nanoparticle electrode.

FIG. 11 Measurement of the intrinsic outward current of CHO cells through conductive nanoparticles penetrating the cell membrane of CHO cells cultured on a conductive plate electrode (by the membrane voltage clamp method).

DESCRIPTION OF EMBODIMENTS

Figure 1:
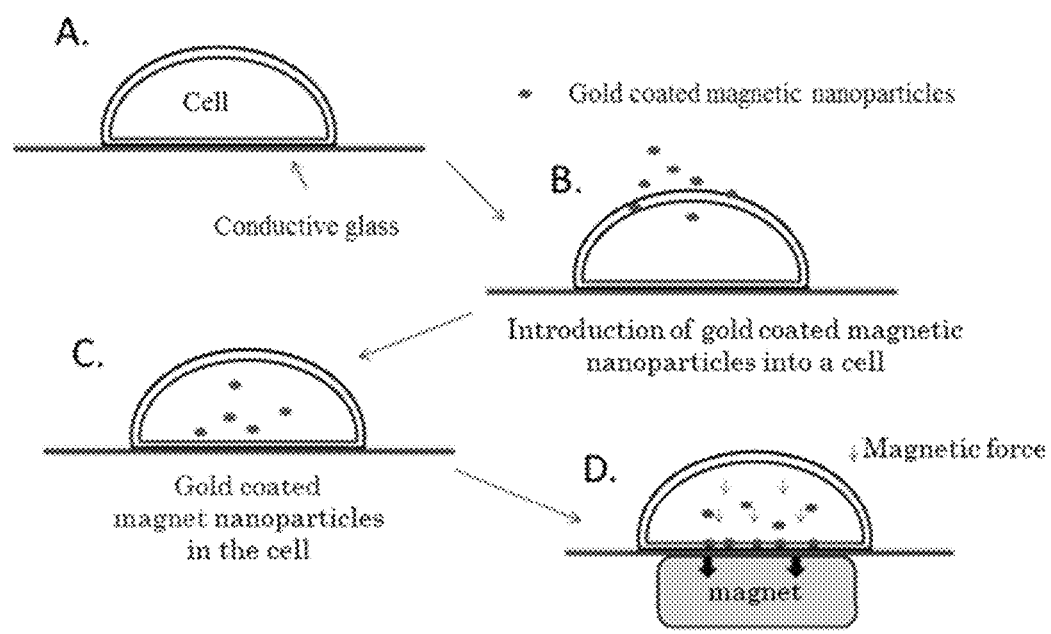
FIG. 1 (A) to (C): A procedure for introducing gold-coated magnetic nanoparticles into cells, (D): A conceptual view showing a procedure for attracting gold-coated magnetic nanoparticles in cells by a magnet under a conductive glass surface.

1. Basic Method of the Present Invention
(1-1) Basic Principle of the Present Invention The basic principle of the present invention is that the conductive nanoparticles previously introduced into the cell are attracted to the extracellular magnetic field and penetrate the cell membrane, so that the conductive nanoparticles span the cell membrane, one inside the cell and the other. The other one of the cells is exposed to the outside of the cell to act as an intracellular electrode and to measure and record the intracellular potential (or membrane current) outside the cell. At that time, a conductive substance is required which constitutes an intracellular recording electrode together with the conductive nanoparticles and serves as a connector for connecting the extracellularly exposed portion of the conductive nanoparticles to the amplifier. One of the electrodes made of such a conductive substance is a plate in which at least a part of the bottom surface of a cell potential measurement container (usually also serving as a cell culture container) for seeding cells has conductivity, and the cell adhesion surface. And the other is a "magnetic electrode" (typically a neodymium magnet) coated with a conductive coating. In any case, by contacting the conductive nanoparticles penetrating the cell membrane, it functions as a part of the intracellular recording electrode to enable intracellular potential recording. Electric potential measurement circuit connected to an electric signal measuring instrument through an electric signal amplifier together with extracellular electrodes (earth electrode) provided in an ionic substance-containing solution (usually, physiological saline) in a cell potential measuring container and measure and record the action potential in cells. Then, if necessary, the intracellular potential is controlled and regulated by an external electrical signal to the extracellular electrode.

In addition, when using a magnet electrode, even if electroconductive nanoparticles are not introduced in a cell in advance, the magnet electrode (electroconductive nanoparticle adsorbed to the magnet coated with conductive material), when pressed against the cell surface, can penetrate the cell membrane and the intracellular potential recording electrode can be made non-invasively. The magnet electrode placed on a metal plate susceptible to magnetic force not only presses the cells below but also is carried out from the opposite side of a cell. The cell membrane can be penetrated by aspiration with the cell. The magnetic force of the magnet electrode not only allows the magnet electrode to press against the cells but also aids the magnet electrode to stand without any help of manipulator.

Hereinafter, first, a general method for using a conductive plate electrode as a part of an intracellular recording electrode (adapter of conductive nanoparticles) will be described, and then, a case where a magnet electrode (adapter of conductive nanoparticles) is explained.

(1-2) In the Case of Using a Conductive Plate Electrode

Here the method that is applied to a cell population (cell sheet) is described; but the method of the present invention is not limited thereto.

(Step 1) Seed test cells on a culture dish or plate at least the surface of which has conductivity (hereinafter referred to simply as conductive plate), and culture the cells until the cells adhere and cover the conductive plate surface tightly. Alternatively, the tissue section is attached to the surface of the conductive plate.

The "conductive plate" does not have to constitute the entire bottom surface of the culture vessel, and may constitute a partial region of the bottom surface. For example, it can be formed by conductive coating only on the cell adhesion surface on the glass surface of the culture dish using a conductive material. As a conductive material for forming the conductive plate region, FTO (fluorine-doped tin oxide) or the like is preferably used, but the present invention is not limited to this as long as the same conditions are satisfied.

At the time of measurement, it is confirmed that the conductive plate covered with the test cells is filled with a sufficient amount of physiological saline and that the conductive surface is not exposed to the extracellular fluid.

Here, it is preferable to use a transparent substrate, such as conductive glass, as the conductive plate for seeding the cells, since the seeding state of the cells can be easily and accurately confirmed with a microscope. In the examples in the present specification, conductive glass (Kenith Co., Ltd.) was used, but the present invention is not limited thereto.

In addition, as a conductive plate, a titanium plate used for culture of osteoblasts and the like (Rosa and Beloti (2003) Effect of cp Ti Surface Roughness on Human Bone Marrow Cell Attachment, Proliferation, and Differentiation. Braz Dent J 14 (1): 16-21) and the like are also preferable. Although there is non-transparency (do not transmit light), Titanium plates have little cytotoxicity, and more conductive than conductive glass, and errors due to series resistance such as conductive glass (with an electrical resistance of 20 to 40 ohms). Titanium plates or non-toxic conductive metals are preferred, especially if accurate measurements are required, as they do not occur.

(Step 2) Nanomagnetic particles (particle size 25 to 100 nm) coated with a conductive material are introduced into cells. In the present invention, "nanomagnetic particles coated with a conductive material" may be simply referred to as "conductive nanoparticles".

Here, a typical conductive material used in the present invention is a conductive metal such as gold or platinum. Any conductive material that can be coated as described in the above can be substituted.

(Step 3) The conductive nanoparticles taken into cells are attracted by a magnet (neodymium magnet, conductive magnet, etc.) placed below the culture dish to penetrate the cell membrane below the cells.

(Step 4) Connect the conductive plate to the (+) electrode of the amplification amplifier, connect the ground provided in the solution to the (−) electrode, and measure the intracellular potential with an extracellular recording device. Since the conductive nanoparticles are larger than the thickness of the cell membrane (about 20 nm), the conductive culture surface of the culture dish (conductive glass electrode) directly reflects the potential in the cell via the conductive nanoparticles. Since the current flows between the cell and the extracellular electrode provided in the extracellular fluid, it becomes possible to record the intracellular potential, the spontaneous fluctuation of the current, and the fluctuation of the potential in response to the stimulation. In addition, if necessary, the intracellular potential can be controlled and regulated by applying a current stimulus between the conductive glass (intracellular space) and the extracellular electrode.

(1-3) Procedure when Applying Gold-Coated Magnetic Nanoparticles to Single Cells (Conceptual Diagram)

The schematic view of the method of the present invention in the case of using the conductive plate is shown in (1-2), where the gold-coated magnetic nanoparticle, which is a typical conductive nanoparticle in the present invention, is applied to a single cell FIG. 1 and FIG. 2) will be described below.

(1) Introduce gold-coated magnetic nanoparticles into cells (FIG. 1A-C).

(2) The gold-coated magnetic nanoparticles are attracted to the surface of the conductive glass by a magnet placed on the opposite side of the conductive glass to which the cells are attached (FIG. 1D).

(3) The gold-coated magnetic nanoparticles attracted to the glass surface by the magnet penetrate the cell membrane of the glass adhesion side of the cell.

(4) Gold-coated magnetic nanoparticles, which penetrate the cell membrane, connect the inside of the cell and the electrode, and the gold coating around the magnetic nanoparticles enables measurement of the potential and current in the cell.

(5) The intracellular potential is measured by the recording electrode, ground, and amplifier arranged as shown in (5) (FIG. 2).

(1-4) Conceptual Diagram when Applied to Cultured Cell Population

When applied to cultured cells and the like in actual experiments, there are usually a plurality of cells. At that time, since the glass surface to be an electrode and the ground are directly connected through the extracellular fluid (in the presence of ionized ions) if the intercellular connection is not tight, the intracellular potential established by the gold-coated magnetic nanoparticles and recording through gold-coated magnetic nanoparticles is not possible because connection between the extracellular solution and bare conductive glass surface will shunt the electrical circuit. For that purpose, it is necessary to spread the cells without gaps on the entire surface of the conductive plate (electrode). The area of the electrode is preferably as narrow as possible (FIG. 3). When the conductive material is drawn in a pattern on the surface of the culture dish to form a conductive plate region, the conductive plate region is formed so as to at least fit within the cell adhesion surface.

(1-5) Method Using Magnet Electrode (MagEle)

A magnet coated with a conductive material (for example, a conductive metal such as nickel or aluminum) can be used as a "magnet electrode (MagEle)" because it has conductivity as well as magnetic force, and a typical one is a neodymium magnet.

A neodymium magnet is the magnet with the highest magnetic force among the permanent magnets, but since it is easily rusted, nickel plating is usually applied. Since a commercially available 1 mm diameter cylindrical neodymium magnet (Neomag Co., Ltd.) is also coated with Ni—Cu—Ni, it has high magnetic conductivity and high conductivity, and can be used as a magnet electrode (MagEle). In addition, aluminum-coated magnet can be used as a magnet electrode (MagEle). Also, the minimum requirement of magnet is being able to generating a magnetic field that can attract conductive nanoparticles in the cell; and is not limited to a neodymium magnet, but is typically an example using a neodymium magnet will be described. Note that the magnet may be placed on the cell or the cell may be placed on the magnet, as long as the conditions for attracting the nanoparticle introduced into the cell to the magnet electrode in contact with the cell are satisfied.

Figure 8:
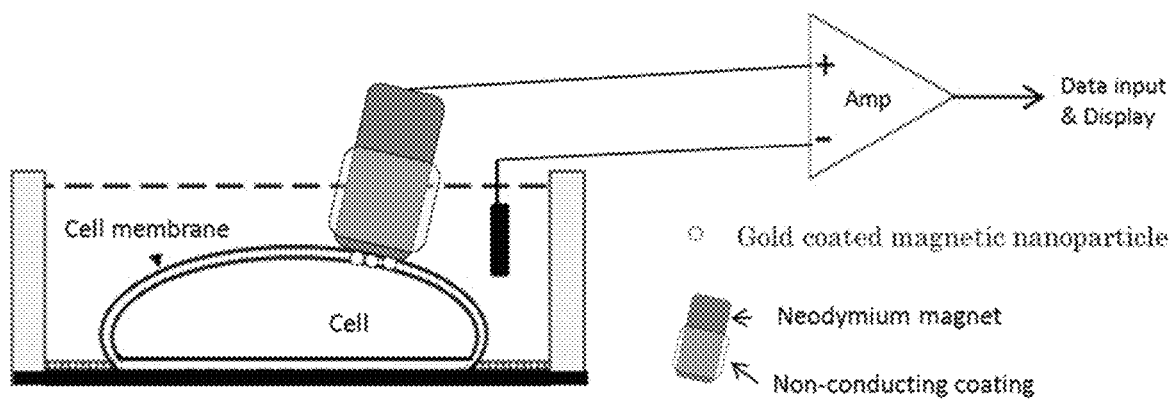

For example, after introducing conductive nanoparticles into cells, place the neodymium magnet on the top of the cells in the solution and pull previously introduced conductive nanoparticles toward the magnet. It results in the penetration of conductive nanoparticles, and the conductive nanoparticles become transmembrane to electrically connect the intracellular space and the extracellular space (magnet surface). Schematic description of the magnet electrode is shown (FIG. 8).

Here, since it is necessary to completely block the extracellular solution from the neodymium magnet surface other than the contact portion with the cell, the insulating coating by silicon rubber, silicon tube etc. is applied in advance except the contact portion with the cell deep. Thus, in the method of using a neodymium magnet as a magnet electrode (MagEle), it is not necessary to place cells on a conductive glass, and a normal culture dish can be used as it is. Therefore, there is an advantage that it is possible to directly record changes in intracellular potential after introducing nanomagnet particles using cells cultured in a culture dish as they are.

Also, cells (cultured cells or cultured cell groups) need not be present in other parts if sufficient contact area with the magnet electrode (MagEle) disposed thereabove can be secured, unlike the method described above, a dish the entire bottom does not have to be covered with cells.

Further alternatively, first the gold-coated magnetic nanoparticles are sufficiently adsorbed on the magnet electrode, and then the surface of the magnet electrode on which the conductive nanoparticles are adsorbed is directed downward, and is placed directly onto the cells in the culture vessel placed on the iron plate. The magnet electrode is fixed on the cell by being drawn to the iron plate below the culture vessel. The nanoparticles adhered to the magnet electrode by magnetism penetrate the cell membrane by the pressure generated by magnetism between the magnet electrode and the lower iron plate. Because the nanoparticle stays in the cell membrane, this method enables intracellular recording. According to the method, the step of introducing conductive nanoparticles into cells in advance is not necessary.

2. Conductive Nanoparticles Used in the Present Invention

In the present invention, the term "conductive nanoparticles" refers to nanoparticle-sized (25 to 100 nm) fine particles having both conductivity and magnetism. In general, it refers to "nanomagnetic particles coated with a conductive material". In general, the conductive nanoparticles used in the present invention are magnetic nanoparticles coated on the surface with a material that is conductive and has close to no cytotoxicity.

As materials suitable for coating at that time, for example, other conductive metals such as gold and platinum (Yamada et al. (2015) WIREs Nanomed Nanobiotechnol 2015, 7: 428-445. Doi: 10.1002/wnan.1322). And conductive peptides and proteins, and various conductive polymers, but not limited thereto. Citric acid or PEG gold coated magnetic nanoparticles (Nanomammunotech, NITmagold Cit or PEG 50 nm) are used in the examples herein, and also in describing the present invention, although primarily described with reference to typical gold-coated nanoparticles, it is not meant to be limiting The magnetic nanoparticles to be used as the core may be any particles as long as they have magnetism, and even if they are not coated particles, they have conductivity as well as nanoparticles having little cytotoxicity. It can be used similarly.

Specifically, as conductive polymers and peptides, as poly (anthranilic acid) with magnetite nanoparticles magnetic properties, and AC and DC conductivity, "Ramesan and Jayakrishnan (2017) Polymer/magnetite nanocomposites with electrical and magnetic materials" Conductive polymers and peptides listed in conductivity. Plastic Research On line 10.2417/spepro.006898 "can be used. In addition, Quantum dot (Qdot) particles (OO Otelaja, D.-H. Ha, T. Ly, H. Zhang, and RD Robinson, "Highly Conductive Cu2-xS Nanoparticle Films, which have been conventionally used for staining of biological imaging. Through Room Temperature Processing, and an Order of Magnification Enhancement of Conductivity via Electrophoretic Deposition, "ACS Applied Materials and Interfaces 6, 18911-18920 (2014)." and the like can also be used as conductive nanoparticles. The diameter of the conductive nanoparticles (50 nm) needs to penetrate the cell membrane and thus needs to be longer than the thickness of the cell membrane (about 20 nm), but the diameter should be as small as possible to minimize cell damage the shorter one is better.

That is, the numerical value range is preferably 25 to 100 nm, preferably 30 to 80 nm, more preferably 35 to 70 nm, and still more preferably 40 to 60 nm. Commercially available gold-coated magnetic nanoparticles (Absolute Mag™ Gold Coated Magnetic Particles, Citrate 50 nm in diameter, manufactured by Creative Diagnostics) (WHM-GC01) may be used.

The conductive nanoparticles of the present invention only have to have the function of penetrating the cell membrane and acting as an electrode, and the shape is not limited to a spherical shape, and may be another shape such as a linear shape. In that case, it is preferable that the maximum length of the particles is in a numerical range of 25 to 100 nm, preferably 30 to 80 nm, more preferably 35 to 70 nm, and still more preferably 40 to 60 nm.

3. Method of Introducing Conductive Nanoparticles into Cells

As a method for introducing the conductive nanoparticles of the present invention into cells, a known method of introducing nanoparticles into cells is described in the review literature "Levy et al. (2010) Gold nanoparticles delivery in mammalian live cells: a Nano reviews, 1: 4889- DOI: 10.3402/nano.v1i0.4889) "may be used, but it is preferable to use a method which minimizes the damage to the cells to be introduced. In Example 1 of this specification, etc., polyethyleneimine solution (P3143 Sigma-Aldrich Mn 60,000) is used as a transfection reagent, and streptolithine O is used as a pore forming protein toxin to cell membranes. It is not limited to the method.

Specifically, for example, the following method can be used.

(1) Method via a protein toxin (such as Streptolysin O) that reversibly forms a pore (a tubular passage through the membrane) on the cell membrane of a target cell:

Protein toxins as pathogenic agents that form pores in the membrane of target cells have long been known, and for these protein toxins, reversible holes are formed while controlling the toxicity to the target cells, a technology that works like non-selective ion channels (pores) has also been developed (Walev et al., PNAS 98: (6) 3185-3190 (2001); T. Tomita., Bio. Soci. Japan General Incorporated Association, Vol. 34, No. 6 (1994) p. 6-11, and the like).

As such a toxin, preferably used is Streptolysin O, which is a type A hemolytic streptococcus, or the alpha toxin of staphylococci bound to a liposome. But not limited to these.

(2) Method Using Transfection Reagent:

As a transfection reagent, Superfect (Qiagen) can be used other than polyethyleneimine (polyethylineimine). Similar to polyethylineimine, Superfect is known to make pores with dendrimer. Since polyethyleneimine with a large molecular weight forms large pores, polyethyleneimine is more effective.

The transfection reagent is used as a typical reagent for introducing conductive nanoparticles into cells in advance, but it is also effective in the following method (5) of penetrating conductive nanoparticles from the outside of the cell to the cell membrane.

(3) Method of Using Intracellular Uptake by Endocytosis:

The drawback of this method is the step of transferring from the endosomal membrane to the cytoplasm after the conductive nanoparticles are taken up into the target cells.

For that purpose, it is preferable to devise, for example, transfer the conductive nanoparticles from the endosomal membrane to the cytoplasm by adding Cell penetrating peptide (CPP) such as TAT and TAT-HA to.

(4) Method of Mechanically Inserting Using a Shot Gun (Genegun) or the Like:

There are two types of methods, a method of introducing conductive nanoparticles into cells and then seeding target cells, and a method of inserting conductive nanoparticles first after seeding target cells.

Either method may be used, but in the case of the former, there is a merit that a commercially available device (Helios® Gene Gun System, Bio-Rad) can be used, so in particular when targeting a large amount of cells and/or conductive nanoparticles.

(5) Method of Permeating Conductive Nanoparticles from the Outside of the Cell to Cell Membrane:

Method of pressing the conductive nanoparticle magnetically fixed to the magnet electrode directly to the cell and inserting and penetrating the cell membrane by the attraction force of the metal plate placed on the opposite side:

Specifically, the conductive nanoparticles are first fixed to the magnet electrode surface by magnetic force. At this time, a mixture of conductive nanoparticles with a transfection reagent represented by PEI (polyethyleneimine) may be used. Subsequently, the magnet electrode is pressed against the surface of the target cell, and the magnet electrode is self-fixed by the magnetic force generated between it and the metal plate provided below the cell. When the magnet electrode is thin and the magnetic force is weak, it may be fixed by a manipulator or the like without depending on the magnetic force with the lower metal plate. A nanoparticle adhered and fixed on a magnet electrode penetrates the cell membrane, and thereby an intracellular recording electrode is formed by the conductive nanoparticle of which one end reaches the cytoplasm and the magnet electrode. At that time, the transfection efficiency is further enhanced by using PEI and other transfection reagents in a mixed state. The method is a very non-invasive procedure as it is not necessary to introduce conductive nanoparticles into the cytoplasm.

Hereinafter, the case of using PEI will be specifically described, but other transfection reagents may be used.

PEG or -Citrate stabilized Au-coated magnetic nanoparticles mixed with PEI are added to the magnet electrode and the nanoparticles are magnetically attracted to the magnet electrode with its side is coated by insulator.

Here, as the insulator, parafilm, silicon, wax or the like can be used, and it is desirable that all parts in contact with the extracellular fluid except the parts to be in contact with the nanoparticles of the magnet electrode be covered. In the case of silicon, it is also possible to use a silicon tube that fits snugly with the magnet.

After about 30 minutes, the surface of the magnet electrode on which the conductive nanoparticle is adsorbed is turned down, brought close from above the cells in the culture vessel, and brought into direct contact with the cells. Note, the culture vessel is placed on a material that can attract a magnet, such as an iron plate. The magnet electrode is fixed on the cell by being attracted to this iron plate. The conductive nanoparticles penetrate the cell membrane with help of PEI. Since one end is attached to a magnet, so it stays in the cell membrane and enables intracellular recording. That is, intracellular recording can be performed without introducing nanoparticles into cells in advance. However, in this method, if the magnet is too weak, it is necessary to hold the magnet electrode with another manipulator etc., so it is necessary to optimize the strength and size of the magnet depending on the type of cells and culture conditions.

4. Device for Measuring Intracellular Potential of the Present Invention or Changes Thereof (4-1) Intracellular Potential Measurement Container In the present invention, a general-purpose culture dish, culture plate, etc. can be used as it is, in the case of using a magnet electrode. Moreover, also when using a conductive plate electrode (as a minimum requirement, at least a part of the bottom of the culture vessel is provided to be conductive), since it can culture cells directly on it, it can use as a culture container. Therefore, in any case, the culture vessel used for seeding and culturing the target cell can be used as it is as a container for measuring the intracellular potential. It is also possible to transfer a cell culture plate from the container to another container for measuring the intracellular potential if it is easier to perform measurement.

When using a conductive plate electrode, cells are seeded to cover about 80% of the dish surface used for recording, and wait until the cells proliferate and become confluent. First the culture is washed several times with physiological saline, and conductive nanoparticles are introduced into the target cells in the culture vessel. After recovery of effects on cells by introduction of nanoparticles by PEI and SLO, intracellular potential or potential change can be measured and recorded by drawing the conductive nanoparticles in the cell to the magnet electrode or conductive plate electrode side by a magnetic field and penetrating the cell membrane.

In the case where dividing cells are used, the number of nanoparticles per cell decreases as the cells divide. Therefore, it is preferable to preform experiments (apply a magnetic field) soon (within a day or two) after the introduction of nanoparticles (after recovery of damage to the cell membrane by introduction of nanoparticles by SLO etc. However, according to the method of introducing nanoparticles (whether introducing nanoparticle to adhered cells or cells in suspension), the timing of applying a magnetic field needs to be adjusted appropriately according to the cell type used. In the case of a magnet electrode, it is more preferable because it is not necessary to cover the bottom surface entirely in the form of a sheet. As long as osmotic pressure and pH are maintained, buffer solutions with different ion compositions can be replaced with the physiological saline for the purpose of experiment (4-2) Use of Instrument for Intracellular Potential Measurements Conductive plate electrode or magnet electrode reflects intracellular potential changes through conductive nanoparticles that penetrate the cell membrane. By detecting the potential differences between those electrodes and ground electrode, provided in the extracellular fluid, spontaneous membrane potential changes and currents in cells and induced potentials and currents can be measured using an amplifier. Since the current and the potential generated are extremely small, in order to record the intracellular potential, a device equipped with an amplifier that increase the sizes of current and voltage is essential.

As such a device, any device conventionally used to measure the intracellular potential or extracellular potential of a cell or a cell group can be used.

Specifically, in the case of a patch clamp amplifier for intracellular recording, an amplifier having a minimum input resistance of $10^6$ to $10^8$ ohms can be used. For example, a patch clamp amplifier (i.e. Axopatch 200A, Axon instruments) can be used.

Moreover, an MEA system can be used, if it is capable of measuring a direct current signal not a alternating current signal).

(4-3) Method of Measuring Membrane Current and Apparatus Therefor

A patch clamp amplifier is used to measure the membrane current (current flowing through the ion channel present in the cell membrane), but in experiments using artificial lipid bilayer membranes, the total membrane capacity is much larger than the size of a single cell capacitance (4-2), it is necessary to use an amplifier that is capable of handling the large capacitance (i.e. Axopatch-1D Patch-clamp amplifier, Axon Instruments) is used. Then, use Voltage clamp mode instead of Current clamp mode when recording cell membrane potential.

The Axopatch 200A (Voltage clamp) used so far is particularly suitable for common patch-clamp experiments to control the membrane potential of a single cell. When used for a large number of cells, Axopatch-1D with the CV-4 Head stage (suitable to measure artificial lipid bilayers) is used because it is necessary to control a large amount of membrane area in order to control membrane potentials. The head stage for an artificial lipid bilayer membrane experiment has the advantage of being able to rapidly charge the lipid bilayer membrane of many cells because it can carry a large current. Further, Bilayer Clamp Amplifier (BC-535) (Warner Instruments) may be used instead of Axopatch-1D Patch-clamp amplifier.

5. Cell Type(s) that the Current Invention can be Applied and Cell Seeding Methods (5-1) Target Cell, Cell Population (Cell Group)

The cells to be measured in the present invention may be cells derived from a living body such as cells collected by biopsy or cultured cells. Although mainly intended to perform measurements from mammalian cells such as humans, it may be from birds, fish, insect cells, eukaryotic microbes such as yeast, and prokaryotic microbes such as *E. coli*.

In particular, this invention is suitable to perform measurements from cardiomyocytes differentiated from human stem cells such as human iPS cells, neurons, vascular epithelial cells, liver cells, etc., or their cell populations.

In addition, transformed mammalian cultured cells, such as HEK and CHO cells, in which various ion channel genes and various transporter genes are introduced are preferred target cells in the present invention because it can be used as an evaluation system in toxicity tests for drugs taken from various ion channels and transporters The current invention is designed to record from a cell population (cell group) grown in cell culture but may be applied to record from a single cell.

In the present invention, the term "cell population" refers to a sheet-like cells formed on the surface of a culture dish (plate, well) for adherent culture, which includes cell clusters formed by cardiomyocytes and nerve cells, etc. derived from stem cells such as iPS cells.

In addition, target cells of the present invention include artificial cells containing large liposomes that have been widely used as model cells in recent years (Moscho et al. (1996) PNAS 93: 11443-11447; Schlesinger Saito (2006), Cell Death and Differentiation 13, 1403-1408; Aimon et al. (2011) PLoS ONE 6 (10): e25529. doi: 10.1371/journal. pone.

For example, artificial cells can be used where artificial cells are giant liposomes that are fused with cell membrane fragments containing ion channels separated from cells expressing ion channels, or with small liposomes incorporating recombinant ion channel proteins expressed in *Escherichia coli*.

The present invention is particularly useful for drug discovery screening using model cardiomyocytes or neurons.

As a cardiomyocyte model, it is preferable to use cardiomyocytes differentiated from stem cells such as human iPS cells or cultured animal cells (HEK 293, BHK, or CHO cells that express SCN5A (Nav1.5), CACNα1C (Cav1.2), KCNH2 (hERG), KCNQ1/KCNE1 (LQT1), KCNJ2 (Kir2.1) genes in the cell membrane or the like are introduced. As such cells, for example, myocardial model cells described in WO2014/192312 can be used.

Also, instead of using the transformed cells, cultured cardiomyocytes derived from stem cells such as iPS cells can be used (WO2014/098182).

Myocardium-like iPS cells (iCell Cardiomyocytes) are also marketed by CDI and others.

A tissue section sample from a living body can also be used, and in this case, a myocardial tissue section that forms an atria or a ventricle from mammalian cells is used to find out causes causing atrial fibrillation and arrhythmia. A piece of tissue or the like removed by biopsy from a diseased tissue can be used.

In addition, as a neuronal cell model, PC12 cells, cerebral cortical cells, and neurons that are derived from iPS cells, in which channelrhodopsin gene product is expressed, can be used. By observing and comparing the potential response induced by the channelrhodopsin that is triggered by blue light stimulation before and after addition of test compounds, it is possible to test toxicity and drug efficacy to nerve cells. As a light sensitive model neuron, a channel opsin 2 expressing cerebral cortical neuron described in JP2006-217866A can also be used.

(5-2) Cell Seeding Method:

In the case of using a magnet electrode (MagEle), it can be cultured in a common culture dish and it is not necessary to cover the entire bottom with cells, so it is sufficient to confirm that it stably proliferates after introducing conductive nanoparticles. However, when the bottom of the culture vessel in contact with the cells is entirely formed of a conductive plate (conductive glass), the conductive glass is used as an electrode, and the earth is placed in the extracellular fluid to form a measurement circuit, cells should be seeded to cover the conductive glass surface.

In the latter case, if the number of seeded cells is simply increased, the cells become too dense, and a sufficient space for the cells to adhere to the conductive glass cannot be secured. Conversely, if the cell density is low, the cells just contact each other, and it takes time to form a sheet and it is difficult to control it.

For example, in the case of animal cells such as HEK cells, 0.1 to $2.0 \times 10^5$ cells/cm$^2$, preferably 0.5 to $1.2 \times 10^5$ cells/cm$^2$ are seeded on the conductive glass.

The conductive glass (electrode) surface in contact with the cells should be as small as possible, since the seeding status of the cultured cells is largely responsible for the success of the experiment. For example, 0.001 to 10 mm$^2$, preferably 0.001 to 1 mm$^2$ (in the case of a circle, a diameter of 2 mm or less, preferably 0.01 to 1.0 mm$^2$) is used as the electrode surface.

In order to narrow the surface of the conductive glass in contact with the cells, collagen may be provided in a grid on the surface of the conductive glass. In particular, it is effective in the case of a cell with weak adhesion to conductive glass such as HEK cells and cultured cardiomyocytes. As fibroblasts such as CHO cells adhere on conductive glass, the above surface treatment is not necessary. It is considered that these fibroblasts spread widely flatly when cultured, and the adhesion surface is large.

When a plurality of electrodes is used as in the case of a probe used in a multi-electrode array, it is expected that the probability of electrodes covered without gaps by cultured cells is high because a large number of electrodes exist. Therefore, when MEA (multi-channel recording amplifier) is used as a recording device, there is a high probability that some electrodes will be completely covered by cells even if all the electrodes are not covered by cells, it is considered that the success rate and the reproducibility of the experiment is improved.

When the conductive plate area is formed not on the entire surface of the bottom of the culture vessel but only on a partial area, the number of cells may be sufficient to cover the area. By setting the conductive plate area to an area smaller than the adhesion area of the target cell, it is also possible to measure the intracellular potential in a single cell.

When a magnet electrode is used as the intracellular recording electrode, as described above, the conductive plate area is not necessary on the bottom of the culture vessel, and the number of cells to be seeded is not limited. Similarly, it is preferable to inoculate 0.1 to $2.0 \times 10^5$ cells/cm$^2$, preferably 0.5 to $1.2 \times 10^5$ cells/cm$^2$. It is also possible to measure the intracellular potential in a single cell, unless the region other than the adhesion surface of the magnet electrode to the target cell is isolated and not in direct contact with the extracellular solution.

6. Application of the Present Invention (6-1) Cell Provided by the Present Invention In the present invention, cells carrying a plurality of conductive nanoparticles penetrating the cell membrane in at least a part of the cell membrane are provided as a single cell or as a cell group.

As the conductive nanoparticles, magnetic nanoparticles coated with a conductive metal such as gold and platinum are preferable, and typically, gold coated magnetic nanoparticles (manufactured by nanoimmunotech, NITmagold Cit or PEG 50 nm) are used.

The cell provided by the present invention is a cell that generates a measurable intracellular action potential, and holds a plurality of conductive nanoparticles that penetrate the cell membrane in a part of the cell membrane, and the magnet via the nanoparticle It can also be provided as a cell in a state in which an intracellular electrode is formed in contact with a conductive plate electrode located on the top surface of the electrode or the magnet.

The cells that generate measurable intracellular action potentials are typically cells that become known cardiomyocyte model cells or nerve cell model cells. Examples of cardiomyocyte model cells include HEK cells stably expressing various ion channels working in cardiomyocytes such as Nav1.5/Kir2.1, mammalian cells such as CHO cells, cardiomyocyte like cells derived from stem cells such as iPS cells, and the like Commercially available Cardiomyocytes including commercially available iCell Cardiomyocyte (CDI) can be applied.

(6-2) Kit for Measuring Action Potential in Cells, Device

The cells provided with conductive nanoparticles penetrating the cell membrane in at least a part of the cell membrane provided in the present invention are, of course, a culture vessel having a conductive plate on at least a part of the bottom as well as in a common culture vessel. Since the cells can be passaged at least once, the cells can be distributed as a kit in which the cells are combined with a conductive plate electrode or a magnet electrode. The term "cell" as used herein includes any cell line already established by gene transfer, or a cell in which nanoparticles have been introduced to a primary cell such as a cultured cardiomyoid cell line or a neural cell line.

Specifically, the cell or cell group of the present invention penetrates the cell membrane in at least a part of the adhesion surface with a magnet electrode in contact with a part of the cell surface or a conductive plate electrode provided in contact with the top surface of the magnet. The kit may be combined with an intracellular recording electrode in contact with the plurality of conductive nanoparticles and, optionally, an earth electrode that can be placed in an extracellular solution.

Furthermore, a kit comprising a cell or cell group of the present invention, an intracellular recording electrode, an earth electrode, and a container for measuring intracellular potential (culture vessel) capable of securing a water depth where cells can be buried in physiological saline solution; Amplifiers, potential or voltage measuring devices can also be combined.

When subculturing cells or cell groups and introducing conductive nanoparticles into cells, it is necessary to provide an optimal environment (known culture components suitable for the target cells are included) for the cell culture. However, when measuring or controlling the intracellular potential, it is desirable that the impurities between the electrodes be as small as possible, and since it is necessary to contain ions, the solution in the culture vessel should be replaced by saline or buffered physiological solution. It should be noted that methods for replacing the solution in the container are known to those who engaging in electrophysiological experiments. Saline or buffer solution may also be added as one of the components of the kit.

(6-3) Drug Discovery Screening

The present invention is particularly useful for drug screening.

The intracellular potential measurement method of the present invention can record the measurement of the cell action potential and the resting membrane potential as the conventional patch clamp method or the auto patch method.

In drug discovery screening, using the above-mentioned model cardiomyocytes and model nerve cells, the influence on the cell function of the test substance, the contractile activity by electrical stimulation, the analysis of electro-physiological characteristic change, etc. can be performed quickly and accurately. As it can be performed, it is effective for evaluating the cytotoxicity and efficacy of the test substance promptly, and for evaluating the test substance.

EXAMPLES

The present invention will be specifically described below by way of Examples, but the present invention is not limited thereto.

Other terms and concepts in the present invention are based on the meanings of terms that are conventionally used in the field, and various techniques used for carrying out the present invention can be easily and surely implemented by those skilled in the art based on known documents and the like, except for a technique that clearly indicates the source. Various analyses were performed applying the methods described in the manuals of, the analytical instruments, reagents or catalogs used.

The contents described in the technical literature, patent publications and patent application specifications cited in this specification shall be referred to as the description of the present invention.

(Example 1) Measurement of Intracellular Potential in CHO Cells Stably Expressing a Channelrhodopsin Channel (ChRWR)

In this example, based on the present invention method, the intracellular potential recording was made from CHO expressing a photoreceptor channel (Channelrhodopsin: ChRWR) where a normal patch clamp amplifier (Axopatch 200A, Axon instruments) was used as a recording device.

(1-1) Construction of ChRWR-CHO Cell Line that Stably Express hChRWR

The receptor channel (ChRWR) is believed to have a seven-transmembrane rhodopsin-like structure and is known to respond upward (depolarization) to 480 nm blue light stimulation.

Wang and colleagues, belonging to Professor Yawo's group, constructed a channelrhodopsin (ChR)-wide receiver (ChRWR) of a chimeric gene from ChR1 and ChR2. The ChRWR gene, was highly expressed in the cell membrane of PC12 cultured cells and cerebral cortical neurons, and the intracellular potential response due to light stimulation was measured using the patch clamp method. The authors reported that nerve cells can be given photosensitivity by expressing channelrhodopsin gene (Wang et al., 2009, J. Biol. Chem. 284(9): 5685-5696., JP2006-217866A).

In this example, using the ChRWR gene (1073 bp) provided by Prof. Yawo, PCR amplification was performed using Phusion DNA polymerase with the following primers.

sense primer: CACTATAGGGAAGCTaccatggctcgga-gaccctggct (SEQ ID NO: 1)

Antisense primer: ATAGAATAGGAAGCTC-TActtgcctgtccctttgttga (SEQ ID NO: 2)

The obtained PCR product was introduced into pD603 (puromycin, DNA 2.0) vector using InFusion HD Cloning kit (TakaraBio) to construct hChRWR expression vector. This hChRWR expression vector was introduced into CHO cells (JCRB cell bank) using transfection reagent (Superfect, Qiagen) to construct hChRWR-CHO stable expression cell line (CHO cells stably expressing the hChRWR gene).

(1-2) Construction of Intracellular Recording Electrode Using Gold-Coated Magnetic Nanoparticles In order to use the gold-coated magnetic nanoparticles as an electrode, the gold-coated magnetic nanoparticles introduced into cells are pulled from below by a magnet and penetrate into the cell membrane. As a result, Gold-coated magnetic nanoparticles are partially exposed to the inside and outside of the cell through the cell membrane. Since the cells are seeded on the extracellular recording electrode, they act as intracellular recording electrodes as the gold-coated magnetic nanoparticles penetrate the cell membrane (FIG. 1).

At that time, the introduction of gold-coated magnetic nanoparticles into CHO cells was carried out using Poly-ethyleneimine (PEI, P3143 Sigma-Aldrich) according to a modified protocol based on the following URL. (https://labs.fccc.edu/yen/docs/PEI %20preparation.pdf)

Specifically, prepare a 10 mg/ml PEI solution (pH7) in advance and filter it with a 0.2 μm filter (Minisart, Sartorius stedim) and store it at −80° C. Add 5 μl of 100 times diluted PEI solution to a mixture of 80 μl of gold-coated magnetic nanoparticles and 20 μl of 5×HBPS (24 mM HEPES+126 mM NaCl, 4 mM KCl, 1 mM $CaCl_2$, 1 mM $MgCl_2$, 10 mM Glucose) and it was incubated for 15 minutes at room temperature.

Then, the cultured hChRWR-CHO cells prepared in (1-1) were washed with serum free DMEM (Sigma-Aldrich) or OptiMEM I (Invitrogen) containing buffer solution (PBS), The solution was replaced with a solution of gold-coated magnetic nanoparticles and incubated in an incubator at 37° C. for 15 minutes.

Thereafter, by making a magnet act from below the conductive glass to which the cultured cells adhere, gold-coated magnetic nanoparticles were pulled down toward the conductive glass and penetrated the cell membrane. Now the set-up to perform the intracellular potential recording was completed. The above description explained the process of how the intracellular electrode was constructed.

The intracellular potential of the cells on the conductive glass is measured by a device composed of a recording electrode, a ground, and an amplifier arranged as shown in (FIG. 2). Cell culture was performed so that the cultured cells were tightly packed in a narrow area (a circular area with a diameter of 1.5-2 mm) on the glass surface so that the glass surface and the ground that served as the electrodes did not directly short-circuit with the extracellular fluid.

(1-3) Measurement of Intracellular Potential by Gold-Coated Magnetic Nanoparticle Electrode The cultured cells containing the intracellular recording electrode constructed in (1-2) were irradiated with blue light, and the amount of the stimulation response was measured (FIG. 4).

In the figure, blue light (irradiated for 12 seconds) was applied every 25 seconds to increase the output intensity of blue light to four levels (Max 1.2A, LED Driver M00290257, 470 nm M470F1, Thorlabs).

Increasing the blue light output from left to right also enhanced the upward potential response (depolarization).

From this result, gold-coated magnetic nanoparticles introduced into cells, that were grown on conductive glass, penetrate the cell membrane and connect with conductive glass. Such conformation has made the intracellular membrane potential measurement possible by using a patch clamp amplifier (an intracellular recording device, Axopatch 200A, Axon instruments) under current-clamp mode.

Also, in the present invention, unlike the conventional non-invasive intracellular potential measurement method, stable electrical response could be recorded without decay for at least 30 minutes or more.

(Example 2) Measurement of Intracellular Membrane Potential in HEK Cells Stably Expressing Nav1.5/Kir2.1

In this example, measurement of intracellular membrane potential is performed using HEK cells stably expressing Nav1.5/Kir2.1 that spontaneously generate action potentials.

(2-1) Generation of HEK Cells Stably Expressing Nav1.5/Kir2.1

HEK cells (JCRB cell bank) were transformed with vectors using the Nav1.5 and Kir2.1 gene to generate HEK cells stably expressing Nav1.5/Kir2.1.

Specifically, first, the human Nav1.5α subunit gene was excised from the shuttle vector (SCNA5, BC140813: SourceBioscience) and was inserted into pcDNA3.1 (−) vector, hygromycin (Invitrogen).

Since BC140813 is a Nav1.5 gene of Embryonic type, it was replaced with the Nav1.5 gene expressed in human adult cardiac muscle by PCR using human heart cDNA (Zymogen).

The Kir2.1 (NM_000891, KCNJ2) gene (1284 bp) was cloned from total RNA extracted from iPS cell-derived cardiomyocytes (CDI, Cellular Dynamics International) by using Nesting PCR approach with the following primer sets.

Kir2.1 1st sense: CCAAAGCAGAAGCACTGGAG (SEQ ID NO: 3)

Kir2.1 1st A/S: CTTTGAAACCATTGTGCTTGCC (SEQ ID NO: 4)

Since the PCR product could not be confirmed in the first round PCR using the above primer, this First round PCR reaction was diluted 100 times and further PCR was performed using this dilution as a template to obtain the Kir2.1 gene.

Kir2.1 ICR HindIII sense: CACTATAGGGAAGCTACC atgggcagtgtgcgaaccaac (SEQ ID NO: 5)

Kir2.1 ICR HindIII A/S: ATAGAATAGGAAGCT tcatatctccgactctcgccg (SEQ ID NO: 6)

The resulting Kir2.1 PCR product was inserted into the HindIII site of pD608 (blasticidin, DNA2.0).

Kir2.1 gene (Kir2.1 2 ug/ml blasticidin) together with the Nav1.5 gene (50 ug/ml hygromycin) was introduced into HEK293 cells (culture medium, DMEM, Sigma-Aldrich, 10% FBS), and Nav 1.5/Kir2.1 stable expression HEK cell line of was created.

(2-2) Measurement of Intracellular Membrane Potential

When HEK cells, cultured (culture medium: DMEM, Sigma-Aldrich, 10% FBS) as in (Example 1) and covered almost all the surface of the glass surface, gold coated magnetic nanoparticles in diluted PEI solution were introduced into the HEK cells. The cells were incubated at 37° C. for 15 minutes on the measurement glass surface. The intracellular recording electrode made of gold-coated magnetic nanoparticles was constructed by applying a magnet from the lower surface of the measurement glass.

Figure 5:
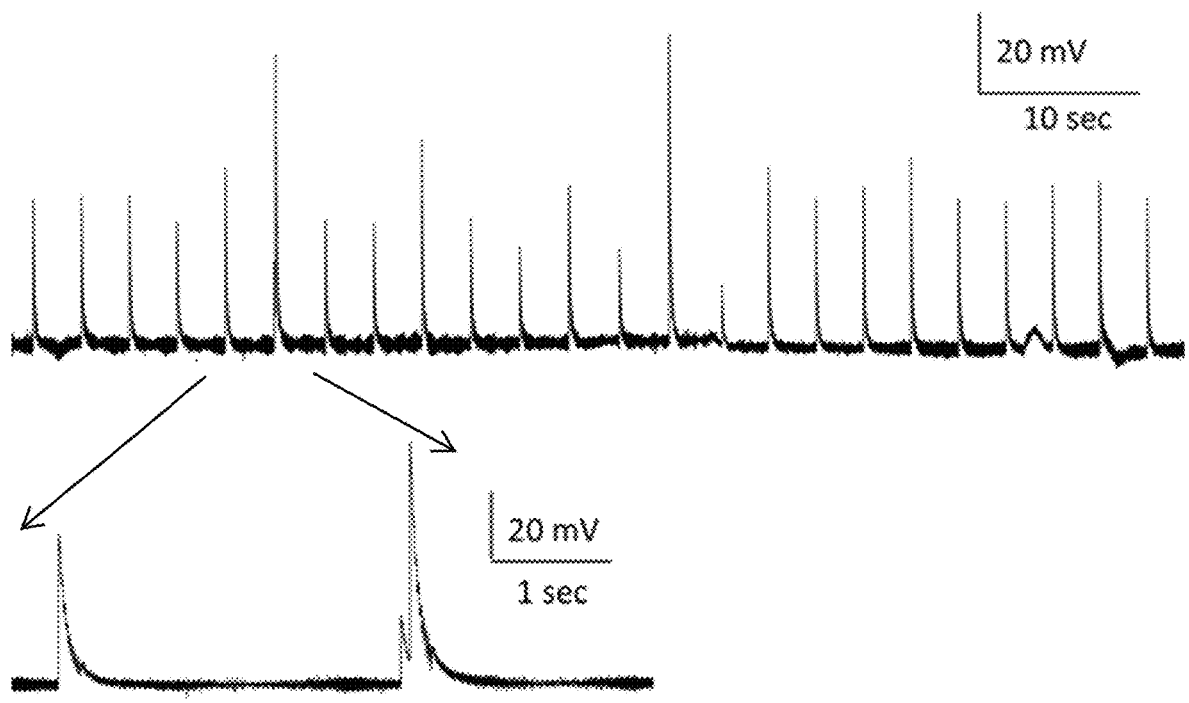
FIG. 5 Measurement of intracellular action potential in Nav1.5/Kir2.1-expressing HEK cultured cells with a gold-coated magnetic nanoparticle electrode (induction of action potential by membrane potential change).

As a result of recording the intracellular potential, the action potential could be stably recorded as a change in membrane potential from 60 mV to 80 mV (FIG. 5).

Figure 6:
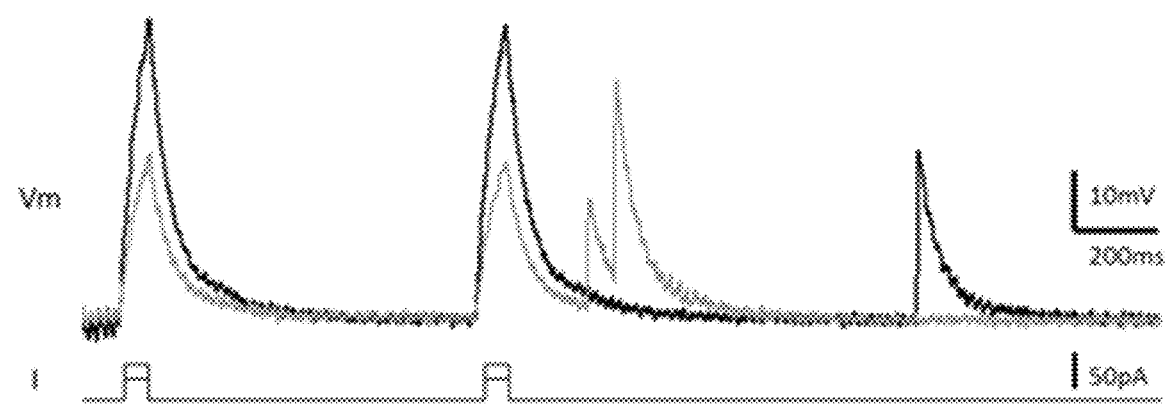
FIG. 6 Measurement of intracellular action potential in Nav1.5/Kir2.1-expressing HEK cultured cells with a gold-coated magnetic nanoparticle electrode (induction of action potential by current pulse).

Similarly, the intracellular potential could be recorded even if the action potential was induced by applying a current pulse (FIG. 6).

(Example 3) Electrophysiological Evaluation of Nav1.5/Kir2.1 HEK Cells

In this example, HEK cells stably expressing Nav1.5/Kir2.1 used in (Example 2) were examined using the patch clamp method, and its electrophysiological properties were evaluated. The results verified the method of the present invention The compositions of the extracellular fluid and intracellular fluid used are as follows.

Extracellular fluid: 126 mM NaCl, 4 mM KCl, 1.8 mM $CaCl_2$), 1 mM $MgCl_2$, 24 mM HEPES, and 10 mM glucose (pH 7.4 NaOH)

Intracellular solution: 130 mM KCl, 5 mM $MgCl_2$, 5 mM EGTA, 4 mM Tris-ATP, and 10 mM HEPES (pH 7.2 KOH)

(3-1) Verification Using Current-Clamp

Figure 7:
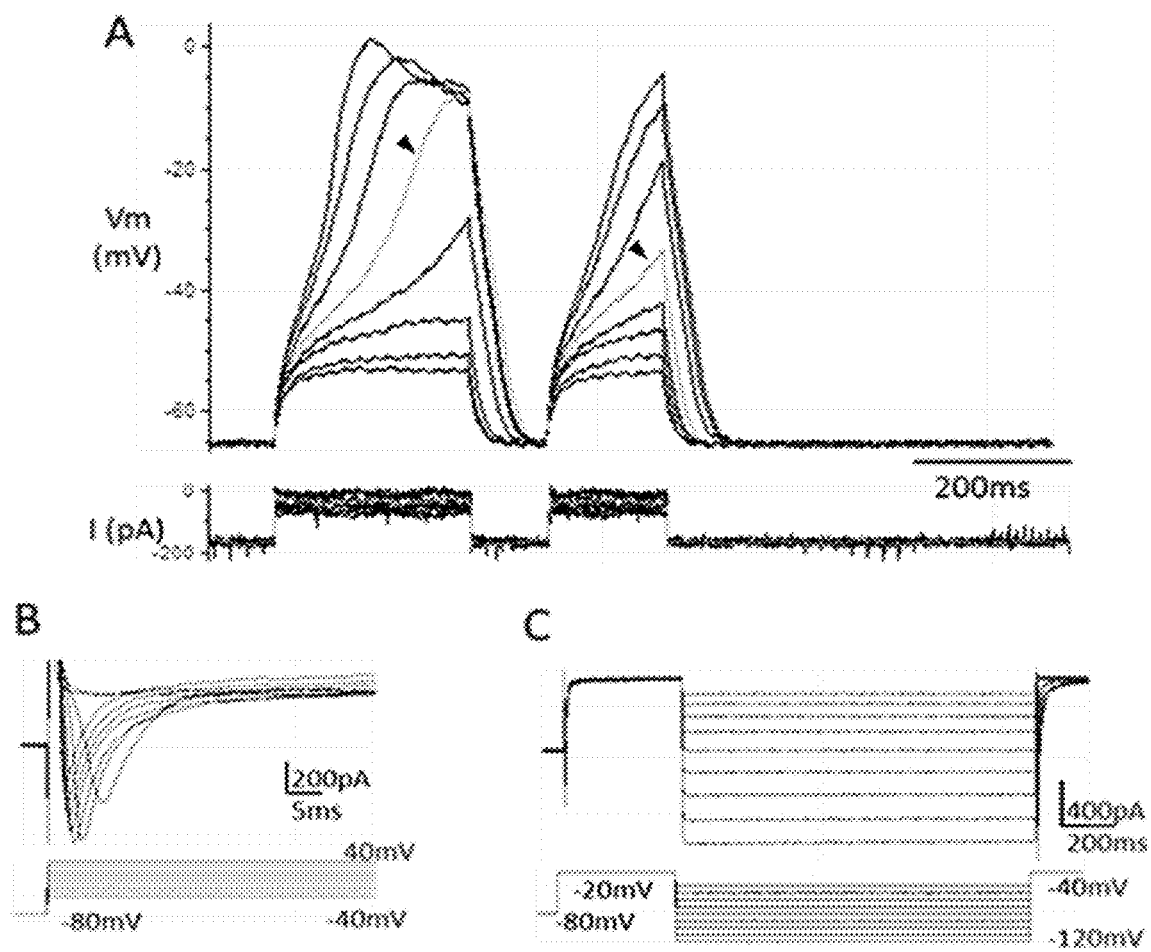
FIG. 7 Demonstration that action potential recording measured in (Example 2) is due to expression of Nav1.5/Kir2.1: (A) Verification by Current-clamp, (B, C) Verification by Voltage-clamp FIG. 8 The conceptual diagram which shows measuring an intracellular electric potential using a neodymium magnet as a magnet electrode. In fact, the magnet is larger than cells, and the lower surface of the magnet adheres to the surface of a plurality of cells.

With respect to HEK cells stably expressing Nav1.5/Kir2.1 used in (Example 2), the cells were stimulated by Current injection, and intracellular potential-like changes in membrane potential were recorded (FIG. 7A). In the figure, the upper (Vm) trace shows changes in membrane potential, and the lower (I) trace shows the amount of applied current. Membrane potential response that was passive when the applied current was small became a self-regenerative potential (action potential), that obeyed all or nothing law due to Nav1.5 activity, when the applied current was increased stepwise. Nav1.5 inactivates immediately after the activation and goes into the inactivation state (refractory phase). This state continues until Nav1.5 recovers from inactivation. The response to the second stimulation is significantly reduced compared to the response to the first current stimulation as shown by the black arrow (arrow head). This strongly suggests that the self-regenerative (activity) potential is caused by the activation of the Nav1.5 channels (FIG. 7A).

(3-2) Verification Using Voltage-Clamp

<Nav1.5 Current (FIG. 7B)>

The membrane potential was fixed at −80 mV (Holding potential), and the potential was increased stepwise from −40 mV to 40 mV in 10 mV intervals from the holding membrane potential. In response to the voltage stimuli, a family of transient inward sodium currents was recorded due to Nav1.5 activity (FIG. 7B).

<KCNJ2 (Kir2.1) Current (FIG. 7C)>

The membrane potential was held at −80 mV. The membrane potential was changed from −20 mV to −120 mV stepwise in 20 mV intervals to activate Kir2.1. From this experiment, the presence of Kir2.1 current was confirmed in this cell line. The transient Nav1.5 current was observed immediately after changing the membrane potential to −20 mV as was seen in the case of the Nav1.5 current experiments (FIG. 7B). Subsequently, the membrane potential-dependent inactivation process of the Nav1.5 current was also observed at −20 mV stimulation pulse. Subsequently, the membrane potential-dependent inactivation process of the Nav1.5 current was also observed by transferring the membrane potential to −20 mV.

As a result of the above-described verification by the patch clamp method, the cells used in (Example 2) can stably express Nav1.5 and Kir2.1. It was confirmed that the measured value in (Example 2) was a measured value of action potential that was originated from Nav1.5/Kir2.1 expression. This indicates that the present invention makes it possible to measure the intracellular membrane potential with simpler operation than the conventional patch clamp method.

(Example 4) Method of Introducing Conductive Nanoparticles Using a Method of Making Pores in the Cell Membrane with Protein Toxin In the present example, gold-coated magnetic nanoparticles were introduced into cultured cells according to the following method, which was modified based on the method of Walev et al. (PNAS 98: (6) 3185-3190 (2001)) using Streptolysin O.

First, Streptolysin O (SLO) (manufactured by Wako Pure Chemical Industries, Ltd.) was activated by reducing it using DTT and the SLO concentration was adjusted to about 5 U/μl.

Then, the solution, contained 40 μl gold coated magnetic nanoparticle, 20 μl 5×HBPS (1 mM $Ca^{2+}$, 1 mM Mg2+), 80 μl dd$H_2O$, was used to resuspend CHO or HEK cells ($2.5 \times 10^6$). 1 ul of SLO solution was added this mixture and it was incubated for 10 minutes at 37° C. By this procedure SLO not only formed pores on the cell membranes but also the pores allowed delivery of the gold-coated magnetic nanoparticles into the cells.

Inactivation (closing) of the SLO pore was completed by mixing the cell-containing solution with 500-1000 μl of DMEM 10% FBS and incubating at 37° C. for at least 20 minutes. Presence of multiple gold-coated magnetic nanoparticle aggregates into the cells were confirmed under a microscope.

From the above, it was confirmed that conductive nanoparticles can be introduced into cells even by the method using protein toxins.

(5-1) A Method of Pulling Conductive Nanoparticles in Cells Toward the Upper Magnet Electrode and Penetrating the Cell Membrane In this example, an intracellular recording electrode is constructed using a 1 mm diameter cylindrical neodymium magnet (Neomag Corporation) coated with Ni—Cu—Ni as a magnet electrode (MagEle). Using "Nav1.5/Kir2.1 stable expression HEK cells" prepared in Example 2, the gold-coated magnetic nanoparticles introduced into cells are pulled toward the magnet electrode by the neodymium magnet electrode (MagEle) plated above the cell. Finally, the gold-coated magnetic nanoparticles penetrated the cell membrane and functioned as an intracellular recording electrode. By using it, the intracellular potential change is recorded (FIG. 8).

Specifically, "Nav1.5/Kir2.1 stable expression HEK cells" prepared in (Example 2) were cultured in a common culture dish using DMEM (Sigma-Aldrich) that contained 10% FBS (BioWest).

Figure 10:
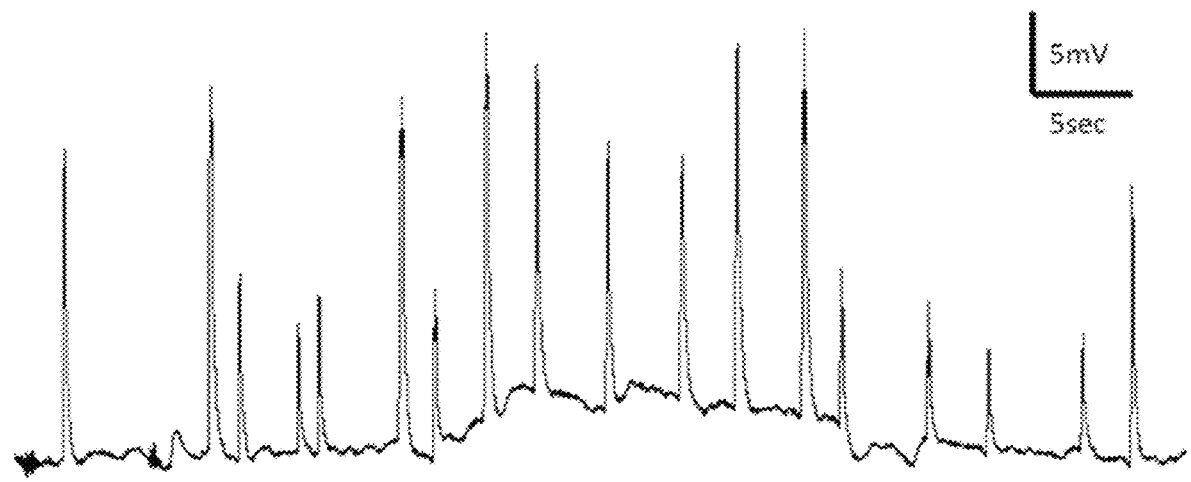

As in (Example 1), gold-coated magnetic nanoparticles were introduced into cells using a PEI diluted solution. For nanoparticle introduction, SLO may be used as in (Example 4). The gold-coated magnetic nanoparticles introduced into the cells were pulled toward the neodymium magnet electrode (MagEle) placed above the cells, the cell membrane was penetrated to construct the intracellular recording electrode, and the intracellular potential change was recorded (FIG. 10).

(5-2) A Method of Penetrating the Cell Membrane with the Conductive Nanoparticle Adsorbed to the Magnet Electrode.

Gold-coated magnetic nanoparticles (Nanomamunotech, NITmagold Cit) mixed with PEI solution were added to the surface of the magnetic electrode, which the side surface was coated with an insulator, and the nanoparticles were adsorbed on the magnetic electrode for about 30 minutes.

Figure 9:
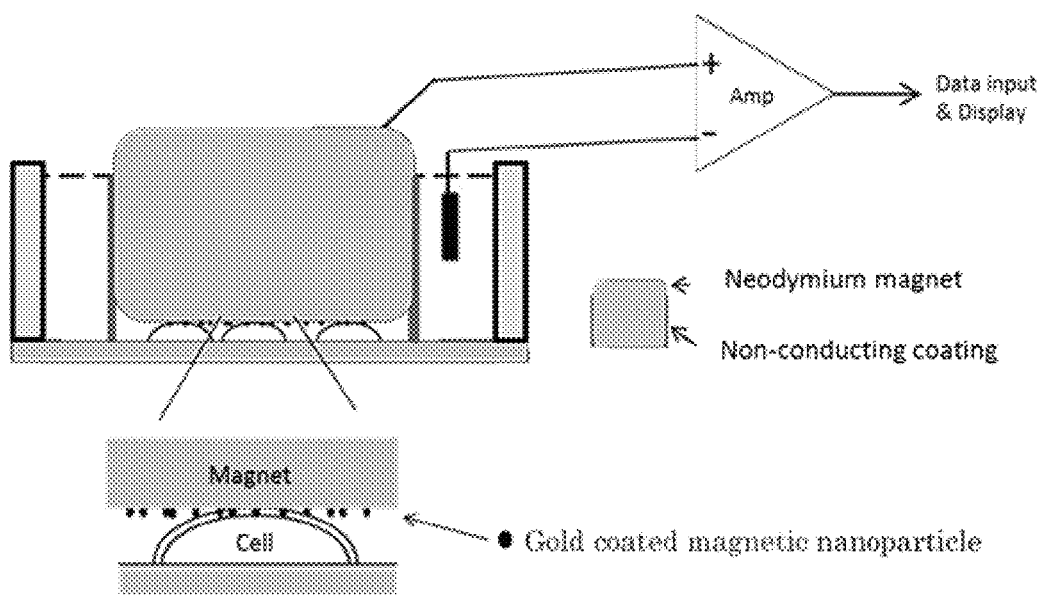
FIG. 9 Conceptual diagram showing that neodymium magnets are used to penetrate cell membranes without introducing gold-coated magnetic nanoparticles into cells FIG. 10 Measurement of intracellular action potential in Nav1.5/Kir2.1-expressing HEK cultured cells having a neodymium magnet electrode (induction of action potential by membrane potential change)

In a culture dish placed on an iron plate, the magnetic electrode was aimed downward from the top to make direct contact with Nav1.5/Kir2.1 HEK cells or cultured myocardial cells (iCell cardiomyocytes). The magnet electrode pulled the iron plate below the culture dish and fixed itself on the cell, and the conductive nanoparticles penetrated the cell membrane through the PEI and were observed to stay inside the cell membrane by the magnetic force of the magnet electrode (FIG. 9).

Furthermore, in any of the cells, the intracellular potential change could be recorded by the intracellular recording electrode (magnet electrode) as in (5-1) (FIG. 10).

That is, even if there is no step of introducing conductive nanoparticles into cells in advance, intracellular recording electrodes can be constructed by a very non-invasive method based on the process of adsorbing a mixture of conductive nanoparticles and PEI to a magnet electrode and pressing it onto cells. It was confirmed that intracellular potential changes could be recorded by using the electrode described above.

In order to confirm whether the aid of PEI as a transfection reagent is necessary when the gold-coated magnetic nanoparticles on the surface of the magnet electrode penetrate the cell membrane, the same experiment was performed by adding only the gold-coated magnetic nanoparticles to the surface of the magnet electrode without mixing with PEI.

As a result, although the number of particles penetrating the cell membrane was smaller compared with the case where it was mixed and used with PEI, and the measured amount of change in intracellular potential was small, it was confirmed that sufficiently distinguishable recordings were possible (data not shown).

(Example 6) in Intracellular Potential Measurement Method in Cells with Weak Adhesion to Conductive Glass Surface Normal animal cells such as CHO cells adhere efficiently to the surface of conductive glass, but some cells such as cardiomyocytes and HEK cells have extremely low adhesion efficiency to the surface of conductive glass. When such cells are seeded directly on the conductive glass surface, it is extremely difficult to culture the cells to cover the entire surface of the conductive glass that constitutes the bottom of the culture vessel.

Therefore, collagen is applied in a grid form on the surface of the conductive glass in advance, and cells are seeded and cultured until the entire surface is covered. Where there is no collagen coating, direct contact of conductive nanoparticles penetrating the cell membrane with conductive glass becomes possible.

Although collagen has low conductivity, it has high cell adhesion and high adhesion to conductive glass, so it is possible to improve the cell adhesion rate at a collagen coating film location. Other examples of such substances include fibronectin and poly-L-lycine, which can be used in place of collagen.

Thereafter, conductive nanoparticles can be introduced into the cells to penetrate the cell membrane in the same manner as in Examples 1, 2 or 4 to construct an intracellular recording electrode. Intracellular potential can be measured using the procedure described above.

(Example 7) Measurement of the Intrinsic Outward Current of CHO Cells Through Conductive Nanoparticles Penetrating the Cell Membrane of CHO Cells Cultured on a Conductive Plate Electrode Using the Membrane Voltage Clamp Method The present example is an experiment for confirming that the cell membrane current generated in the cell can be measured as well as the intracellular potential by using the intracellular recording electrode of the present invention.

CHO cells are cultured in Minimum Essential Medium Eagle (Sigma-Aldrich), 10% FBS (BioWest), 40 mM L-glutamine (Wako Pure Chemical Industries). Streptolysin O (SLO) (Wako Pure Chemical Industries, Ltd.) and was reduced using DTT then activated. The SLO concentration was adjusted to about 5U/µl.

20 µl of gold-coated magnetic nanoparticles and a gold-coated magnetic nanoparticle introduction solution (5 µl 5×HBPS (1 mM $Ca^{2+}$*, 1 mM $Mg^{2+}$), 1 µl SLO were used to resuspend 5×10$^5$ CHO cells (incubated for 10 minutes at 37° C.) to introduce gold-coated magnetic nanoparticles to CHO cells. SLO was inactivated using 5-10 times the volume of FBS containing CHO culture medium. The volume of the culture medium was adjusted using centrifuge and the CHO cells were seeded on conductive glass. When the entire surface of the glass surface was covered, recording of cell membrane current by gold-coated magnetic nanoparticles was performed using the voltage-clamp method. Before the experiment, CHO medium (Minimum Essential Medium Eagle (Sigma-Aldrich), 10% FBS (BioWest), 40 mM L-glutamine (Wako Pure Chemical Industries) was replaced with extracellular solution (24 mM HEPES+126 mM NaCl, 4 mM KCl, 1 mM $CaCl_2$), 1 mM $MgCl_2$, 10 mM Glucose). The membrane voltage clamp method was performed using Axopatch 1D (Axon Instruments) with the headstage (CV-4) used for an experiment on an artificial lipid membrane. The reason for this is that hundreds of cells are cultured on conductive glass. In the voltage-clamp method, in order to control the membrane potential, it is necessary to charge a capacitance of the lipid membrane of the cells. For that purpose, it is necessary to have a Voltage clamp Amplifier that can inject a large amount of current instantaneously.

The following protocol was used for the voltage clamp experiments. The membrane potential is held at −80 mV, and the membrane potential was applied in stepwise from −60, −50, −30, −10, 10, 30, 50 to 60 mV and the pulse duration was 1.4 seconds in length. Then, it was followed by a −40 mV, 400 ms potential pulse (FIG. 11A lower). Outward currents were observed in response to stimulation voltage pulses (FIG. 11A top). The amplitude of the current was measured at each point of Transient and Sustained in FIG. 11A indicated by arrows, and the relationship between the current (vertical axis, pA)–voltage (horizontal axis, mV) was shown in FIG. 11B.

INDUSTRIAL APPLICABILITY

The present invention is particularly useful for drug discovery screening because the intracellular potential can be measured conveniently and accurately. It is expected to make a significant contribution to in vitro electrophysiological research, not only in cultured cardiomyocytes but also in cultured neurons In addition, since the present invention has a simple basic principle, it can be supplied relatively inexpensively, and its application to student training of electrophysiology, basic research and the like can be expected.

---

The invention claimed is:

1. An intracellular recording electrode comprising: conductive magnetic nanoparticles penetrating the cell membrane of target cells, and a conductive plate electrode or magnet electrode contacting with the conductive nanoparticles that are extracellularly exposed at the outside of the target cells, wherein the intracellular recoding electrode is configured to record the intracellular potential or potential change of the target cells since the other end of the conductive nanoparticles are exposed to the inside the cell.

2. The intracellular recording electrode according to claim 1,
wherein the conductive plate electrode that contacts with one end of the conductive nanoparticles exposed outside the cell has a magnet attached to the opposite side of the cell contact surface of the conductive plate electrode.

3. The intracellular recording electrode according to claim 1,
wherein the magnet electrode that contacts with one end of the conductive nanoparticles exposed to the outside of the cell is coated with a conductive substance, and all the surfaces of the magnet electrode in contact with the external liquid other than the contact surface with the conductive nanoparticles are further coated with an insulator.

4. The intracellular recording electrode according to claim 1,
wherein magnetic conductive nanoparticles pre-introduced in the target cells are pulled by the magnetic force from a magnet placed on the opposite side of the cell contacting surface of the conductive plate electrode or by the magnetic force from the magnet electrode to penetrate the cell membrane of the target cells to become transmembrane electrodes, and wherein one end of the conductive nanoparticles exposed extracellularly are in contact with the conductive plate electrode or the magnet electrode.

5. The intracellular recording electrode according claim 1,
wherein at the contacting surface where the target cells and the magnet electrode fixed above the target cells make contact, the conductive nanoparticles penetrate the cell membrane and expose their one ends extracellularly, which make contact with the magnet electrode, and the other ends expose intracellularly, and wherein the intracellular recording electrode also includes a container with magnet attracting metal plate mounted under it to which target cells adhere.

6. The intracellular recording electrode according to claim 5,
wherein conductive nanoparticles pre-adsorbed on the surface of the magnet electrode are pressed against the cell surface from the upper side of the target cell as well as are drawn into the cell membrane by the metal plate equipped below the target cells to form the conductive nanoparticles penetrating the cell membrane of the target cell.

7. The intracellular recording electrode according to claim 6,
wherein the conductive nanoparticles pre-adsorbed on the surface of the magnet electrode are prepared using conductive nanoparticles in a pre-mixed with a transfection reagent.

8. A method for measuring and/or controlling the intracellular potential or changes in the intracellular potential of a target cell comprising the following steps (1) to (7):
(1) culturing target cells in a container placed on a metal plate capable of being attracted by magnetic force;
(2) adsorbing conductive nanoparticles to the surface of a magnet electrode;
(3) contacting the surface of the magnet electrode, on which the conductive nanoparticle is adsorbed directly with the upper surface of the target cell in the container;
(4) drawing conductive nanoparticles to the metal plate placed below the container, to which the cell adheres, to penetrate the cell membrane to expose one end of the conductive nanoparticles to the inside of the target cell;
(5) forming the intracellular recording electrode composed of the transmembrane conductive nanoparticles, having one end exposed to the inside of the target cell and the other end exposed to the outside of the target cell, and the magnet electrode that contact with the extracellular end of the conductive nanoparticles;
(6) providing an extracellular ground electrode at a position that is not in contact with cells in physiological saline in the container; and
(7) connecting the intracellular recording electrode and the extracellular ground electrode to the plus and minus inputs of an electrical signal measuring instrument (an electrical signal amplifier), respectively via, and measuring the current or voltage between both electrodes.

9. The method according to claim 8, which further comprising:
a step of controlling an intracellular potential in the target cell by applying current or voltage to the target cell using the electrical signal amplifier, in which the intracellular recording electrode and the extracellular ground electrode are connected,
wherein in the step, the electrical signal amplifier acts as an electric signal generator.

10. The method for measuring and/or controlling the intracellular potential or changes in the intracellular potential of a target cell of claim 8, further comprising using the transmembrane magnetic conductive nanoparticles, wherein the conductive nanoparticles, that penetrate, span the cell membrane, and are held in the cell membrane by the magnetic force.

11. The method according to claim 10,
wherein one end of the conductive nanoparticles are exposed inside the cell, and the other end are exposed outside the cell.

12. The method according to claim 10,
wherein one end of the conductive nanoparticles exposed extracellularly are in contact with a conductive plate electrode or a magnet electrode.

13. The method according to claim 10,
wherein the conductive nanoparticles are composed of magnetic nanoparticles coated with a conductive material.

14. The method according to claim 10,
wherein at least a part of the target cell membrane comprises conductive nanoparticles penetrating said cell membrane.

15. The method according to claim 8,
wherein the method is conducted by the use of an apparatus comprising:
the intracellular recording electrode according to claim 1 is connected to the positive input of a measuring instrument, and
an apparatus in which a ground electrode placed in the extracellular solution of an intracellular potential recording container is connected to the negative input of the measuring instrument,
thereby to form a potential recording circuit.

16. The method according to claim 8,
wherein the method is conducted by the use of an apparatus comprising at least the following (A) to (E):
(A) a container containing saline solution;
(B) the intracellular recording electrode according to claim 1;
(C) extracellular electrodes provided in saline in the container;
(D) an electrical signal measuring and/or generating device; and
(E) an electric signal amplifier.

* * * * *